United States Patent [19]
Rideout

[11] Patent Number: 4,812,449
[45] Date of Patent: Mar. 14, 1989

[54] IN SITU ACTIVE COMPOUND ASSEMBLY

[75] Inventor: Darryl C. Rideout, Del Mar, Calif.

[73] Assignee: Scripps Clinic and Research Foundation, La Jolla, Calif.

[21] Appl. No.: 108,833

[22] Filed: Oct. 14, 1987

Related U.S. Application Data

[63] Continuation-in-part of Ser. No. 906,143, Sep. 11, 1986, abandoned, which is a continuation-in-part of Ser. No. 882,082, Jul. 3, 1985, abandoned.

[30] Foreign Application Priority Data

Jul. 3, 1987 [CA] Canada ............................ 541192
Jul. 6, 1987 [WO] PCT Int'l Appl. ... PCT/US87/01652

[51] Int. Cl.$^4$ ............... A61K 31/33; A61K 31/35; A61K 31/13; A61K 31/175
[52] U.S. Cl. ................... 514/183; 514/454; 514/579; 514/590; 514/634; 514/639; 514/741; 514/855; 514/895; 514/908
[58] Field of Search ............ 514/183, 454, 579, 590, 514/634, 639, 640, 741, 855, 895, 908

[56] References Cited

U.S. PATENT DOCUMENTS 4,200,436  4/1980  Mochida et al. ............. 23/230 B
4,215,102  7/1980  Lee ................................ 424/3
4,460,560  7/1984  Tokes et al. ................. 424/1.1

OTHER PUBLICATIONS

Walker, E. H. Perspectives in Biology and Medicine, 1980, pp. 424–438.

Primary Examiner—John W. Rollins
Attorney, Agent, or Firm—Irell & Manella

[57] ABSTRACT

Differences in microenvironments associated with various cells and other conditions in this environment are used to advantage in effecting the in situ construction of biologically active agents at target locations in preference to surroundings which are desired to be unaffected.

18 Claims, 11 Drawing Sheets

FIG. 6

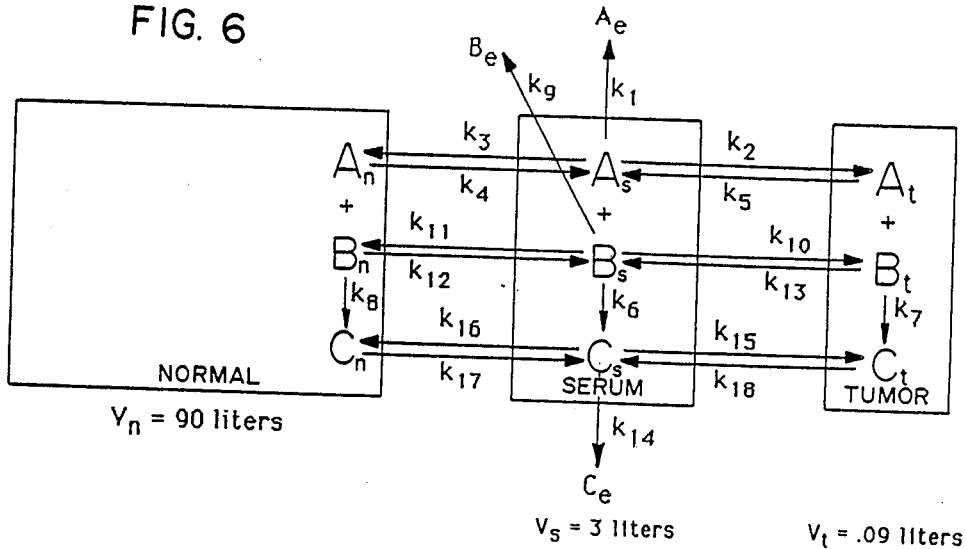

$V_n$ = 90 liters  $V_s$ = 3 liters  $V_t$ = .09 liters $$\frac{dA_s}{dt} = -(k_1+k_2+k_3)A_s + k_4 V_n A_n/V_s + k_5 V_t A_t/V_s - k_6 A_s B_s$$

$$\frac{dA_t}{dt} = k_2 A_s V_s/V_t - k_5 A_t - k_7 A_t B_t$$

$$\frac{dA_n}{dt} = k_3 A_s V_s/V_n - k_4 A_n - k_8 A_n B_n$$

$$\frac{dB_s}{dt} = -(k_9+k_{10}+k_{11})B_s + k_{12} V_n B_n/V_s + k_{13} V_t B_t/V_s - k_6 A_s B_s$$

$$\frac{dB_t}{dt} = k_{10} B_s V_s/V_t - k_{13} B_t - k_7 A_t B_t$$

$$\frac{dB_n}{dt} = k_{11} B_s V_s/V_n - k_{12} B_n - k_8 A_n B_n$$

$$\frac{dC_s}{dt} = -(k_{14}+k_{15}+k_{16})C_s + k_{17} V_n C_n/V_s + k_{18} V_t C_t/C_s + k_6 A_s B_s$$

$$\frac{dC_t}{dt} = k_{15} C_s V_s/V_t - k_{18} C_t + k_7 A_t B_t$$

$$\frac{dC_n}{dt} = k_{16} C_s V_s/V_n - k_{17} C_n + k_8 A_n B_n$$

$$\frac{dA_e}{dt} = k_1 A_s$$

$$\frac{dB_e}{dt} = k_9 B_s$$

$$\frac{dC_e}{dt} = k_{14} C_s$$

SERUM EFFECTS: ERYTHROCYTE LYSIS BY
DECANAL IN THE PRESENCE OF 448 μM AOG
(Self-Assembling Cytotoxin)

$$CH_3(CH_2)_8 CHO \quad + \quad H_2NNHCNH(CH_2)_7 CH_3$$
$$\text{DECANAL} \qquad\qquad \overset{NH}{\underset{}{\|}} \qquad \text{AOG}$$

[Graph: Cells Killed (%) vs Decanal Concentration (micromolar), showing curves for 0% SERUM and 1% SERUM, with MAXIMUM DIFFERENCE = 100%]

1 Hour, 37 °C, pH 6.6, PBS
CONTROLS:
<10% lysis by 896 μM AOG
<5% lysis by 32 μM decanal

FIG. 10a

IN SITU ACTIVE COMPOUND ASSEMBLY

This is a continuation-in-part of U.S. Ser. No. 906,143, filed Sept. 11, 1986, now abandoned, which is a continuation-in-part of U.S. Ser. No. 882,082, filed July 3, 1986 now abandoned.

TECHNICAL FIELD

This invention relates to the formation of biologically active materials in situ. More particularly, it concerns taking advantage of biological microenvironments to permit synthesis of active materials at their target sites.

BACKGROUND ART

The problem of obtaining selectivity in nurturing, or more frequently destroying, certain biological tissues and organisms is well recognized, and mostly unsolved. Examples are legion. One would like to be able to exterminate garden pests without poisoning the cat. One would like to rid the lawn of weeds without killing the grass. It would be desirable to destroy malignant tissue without incapacitating the host's own cells.

Various approaches have been made to this problem. In the most commonly used, an empirical study to determine materials which happen to be more effective with the desired target has resulted in a variety of agents which are inherently selective. While having yielded successful results in some cases, the general method of trial and error does not yield a directed procedure with a high probability of success. At a somewhat more sophisticated level, known differences in metabolism between various target cells can be used to postulate structures for agents which may exhibit differential activity. For example, many antitumor agents are inhibitors of DNA synthesis which are directed to undermining the rapid replication characteristic of tumor cells. This is an example of functional selectivity, which resides in a difference between target and nontarget in sensitivity to a particular substance. Perhaps the most recent approach has been to utilize specific cellular receptors as means to bind particular drugs or toxins to a target cell. This may be regarded as "passive" selectivity, which resides in a difference in the attractiveness of the target environment to a material. In applying this concept, for example, it has been hoped that immunotoxins will become successful as tools in cancer therapy, and that radioactive isotopes bound to, for example, specific antibodies can be targeted to their desired locations.

In the approach described in the present invention a reaction which is at least bimolecular is selectively conducted in the microenvironment of the targeted tissue. Because the assembly of an active reagent from at least two portions (which may or may not be identical) inherently amplifies the selectivity of a microenvironment characterizing the target, quantitative as well as qualitative differences in such microenvironments can be employed. The microenvironment may influence the reaction by concentrating one or more of the components of the reaction at the desired location, by activating one or more of these components, by stabilizing (or not destabilizing) one of the components or the product, or by affecting the rate constant of the reaction which results in assembly of the active product. These are all passive selectivity factors.

It has, of course, been proposed to take advantage of passive selectivity factors directly by targeting specific cells or tissues for the active drug or label in the practice for using immunotoxins or other immunoconjugates as mentioned above. In addition, it has been suggested that passive selectivity factors relating to differential metabolism of pro-drugs in normal and target tissues be employed to effect a differential concentration of the pro-drug in the target tissue, whereupon an activating substance is supplied to release from the pro-drug the active, usually toxic, compound. Walker, E. H. in an article entitled "Chemically Triggered Time-Delay Activation Chemotherapy for the Treatment of Cancer" in *Perspectives in Biology and Medicine* (Spring 1980) pp. 424–438, suggests this concept, designated "triggered time-delay toxin activation", or "TDTA" in connection with tumor therapy. This approach, however, does not envision *assembly* of the active compound, but rather the *release* of the active moiety from the pro-drug. Specific suggestions for such release are, in fact, limited to enzymatic release of functional portions of the pro-drug using later-administered enzyme preparations.

MICROENVIRONMENTAL DIFFERENCES

Tissue-specific and cellular-specific microenvironments have been studied. For example, fluidity at the cellular membrane is quite variable and can significantly affect the rate at which reactions that are at least bimolecular in character can occur. Taraschi, T. F., et al, *Science* (1986) 232: 102, studied the cellular membranes of red cells during malaria infection and found that the membranes were increasingly fluidized as infection progressed. Shinitzky, M., *Biochim Biophys Acta* (1984) 738: 251–261 discusses the changes in membrane lipid fluidity associated with malignant cells. According to this discussion, cholesterol is the main membrane rigidifier in eucaryotes, and thus high levels of cholesterol yield membranes with high levels of microviscosity. Although proliferative activity and membrane fluidity are generally correspondent, the large number of factors which account for the actual fluidity found results in the empirical finding that with few exceptions, tumor cells from solid tissues have lower membrane fluidity than their normal analogs, while tumors of flowing cells have higher membrane fluidity than their normal analogs. In addition, Rintoul, D. A., et al, *Cancer Res* (1984) 44: 4978–4980, have shown that the structural order in the lipid membrane of Chinese hamster lung cells is important to drug resistance or sensitivity. Other work is cited which shows that changes in lipid fluidity of the cell surface affects its adriamycin sensitivity.

This membrane property may have rather finely tuned effects. Wolf, D. E., et al, *Devel Biol* (1981) 85: 133–138; ibid, 81: 195–198, report that the compound

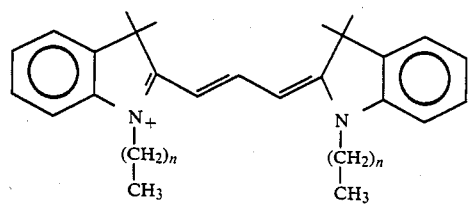

wherein n=15 is more mobile than the corresponding compound where n=21 in fertilized mouse eggs, whereas when the eggs are unfertilized the reverse is true. Thus, assembled molecules are known which can be tailored to correspond to particular environments.

Tumor cells also have other characteristics of interest. For example, Juckett, D. A., et al, *Cancer Research* (1982) 42: 3565-3573, show that sarcoma-180 mouse tumor cells carry nucleic acids on their cellular surfaces; and Carl, P. L., et al, *Proc Natl Acad Sci USA* (1980) 77: 2224-2228, have shown that many types of malignant cells show increased concentrations of the protease plasminogen activator, and are capable of metabolizing pro drugs having the structure D-Val-Leu-Lys-X, wherein X is an anticancer drug. Manson, M. M., et al, *Carcinogenesis* (1981) 2: 661-670 reported that tumor cells have elevated levels of γ-glutamyl transferase (GGT) which was, therefore, suggested to be a diagnostic for malignancy. Bosmann, H. B., *Biochim Biophys Acta* (1972) 264: 339-343, showed cells transformed with retrovirus contained elevated levels of certain glycosidases, which might, for instance, activate glycoside-protected moieties. Bokhari, A., et al, *J Nat Cancer Inst* (1973) 50: 243-247, discloses abnormally low enzyme concentrations generally in tumor cells, which may result in an effective relative stabilization of certain reaction components; Brachwitz et al, *Chem Phys Lipids* (1984) 34: 355-362, reported that some ether lipids are selectively toxic against tumor cells because of abnormally low rates of inactivation in tumor cell membranes.

Sartorelli, A. C. in *New Approaches to the Design of Antineoplastic Agents* (1982) Bardos/Kalman eds., Elsevier Science Publishing Company, pp. 51-57, discusses the design of drugs which are selective for the hypoxic nature of solid tumor cells. Kolata, *Science* (1986) 231: 220 reports on work from a number of groups showing that tumor cells become resistant to anticancer agents by virtue of an enhanced ability to pump them out of the cell's interior. This ability appears to be associated with the presence of abnormally high levels of P-glycoprotein, a 170 kd molecular weight membrane protein; another factor in the cellular microenvironment.

By virtue of surface-contained DNA, certain antitumor agents which bind DNA are selectively bound to tumor cells (Rosenberg, L. S., et al, *Biochemistry* (1986) 25: 1002-1008). Certain cell types also have varying carbohydrate concentrations and a progressive increase in total carbohydrates at the cell surface, notably in the terminal branch sugars, galactose and sialic acid, is found in the transition from normal to neoplastic tissue. (Smetz, L. A., et al, *Biochim Biophys Acta* (1984) 738: 237-249). A recognized metastatic tumor cell characteristic is that of a high anionic charge density, due to the presence of hypersialated glycoproteins, nucleic acids, and anionic lipids (Juckett et al, *Cancer Res* (1982), p. 3573; Sinets et al,, *Biochim Biophys Acta* (1984) 738: 237-249; Roos, ibid, pp. 263-284). In addition, it is known that, for whatever reason, certain materials are preferentially taken up by malignant as opposed to normal cells (Nadakavukaren, K. K., et al, *Cancer Research* (1985) 45: 6093-6099; Abel, G., et al, *Eur J Cancer* (1975) 11: 787-793).

It may be the immediate environment of the cells which reflect their selectivity, rather than the cells themselves. For example, tumor cells are known to be associated with low serum levels, thus decreasing their ability to bind hematoporphyrin derivatives (Bohnen, R. M., et al, *Cancer Res* (1985) 45: 5322-5334).

In addition to the recognition that various cell types offer different microenvironments in their vicinity, it is also known that microenvironments affect the course of particular reactions. For example, UV light-initiated polymerization of diacetylenes is highly sensitive to their conformation (Lopez, E., et al, *J Am Can Soc* (1982) 104: 305-307. The nature of the environment created by the presence of certain surfactants influenced greatly the rate of reaction between nickel ion and pyridine-2-azo-p-dimethylanaline (Jobe, D. J., et al, *Aust J Chem* (1984) 37: 1593-1599).

In general, then, it is clear that various types of cells and tissue offer different kinds of environments at their surfaces. This results in differences in the ability of these cells to offer friendly environments to particular materials, and the nature of these microenvironments influences the course of reactions carried out within them. The present invention takes advantage of these differences, and further magnifies them by making use of their effects on multimolecular, at least bimolecular, reactions to form desired products which influence the vicinal cells, tissues or organisms.

The selectivity of the present invention resides in the selectivity of the microenvironment for components of a reaction which results in a product having a desired biological effect and the automatic amplification of this selectivity when the reaction to form the biologically active product is dependent on a power greater than one for only a single component concentration. It also resides in the variations in rate constant available in various environments and in the intrinsic dose-response curve modification resulting from multiple components.

SELF-ASSEMBLY OF BIOLOGICALLY ACTIVE MATERIALS

There are many instances in which biologically active compounds are formed in the laboratory from inactive reactants. Most synthetic toxic or beneficial biological materials are ordinarily synthesized from smaller components with relatively little, or at least different, activity. For example, some polymers show increased toxicity over their monomeric or multimeric components. The antineoplastic activity of poly-(L-lysine) in some tumors has been reported by Arnold, L. J., Jr., et al, *Proc Natl Acad Sci USA* (1979) 3246-3450, wherein poly-(L-lysine) of Mr 3 kd has less than 1/20 the toxicity of poly-(L-lysine) having Mr of 70 kd on a weight basis. The bis-intercalator, 1,6-bis(9-acridinylamino)-hexane, is active in vitro against leukemic cell lines which have become resistant to mono-intercalators (Johnson, R. K., et al, *Eur J Cancer Clin Oncol* (1982) 18: 179). Two anthracycline molecules linked through a bis-hydrazone produce a bis-anthracycline, exhibiting enhanced ability to inhibit DNA replication (Apple, M. A., et al, European Patent Application, *Chem Abstr* (1980) 92: 164253k). Bis(1,8-anilino-naphthalenesulfonate) is a potent inhibitor of microtubule assembly, while the corresponding monomer, 1,8-anilinonaphthalene sulfonate, is inactive (Horowitz et al, *J Biol Chem* (1984) 239: 14647). Methotrexate oligoglutamates form more rapidly in tumor than in normal cells. They are equipotent with methotrexate as DHFR inhibitors, but are secreted more slowly from the cell. They are more potent as phosphoribosylaminoimidazole-carboxamide transformylase inhibitors (Allegra C. J. et al, *Proc Natl Acad Sci USA* (1985) 82: 4881-4885; Jolivet J. et al, *J Clin Invest* (1983) 72: 773-778). The tridentate chelating agent 2,2',6,6' tripyridine is more cytotoxic to L1210 cells in vivo than the bidentate 2,2'-bipyridine (McFadyen, W. D., et al, *J Med Chem* (1985) 28: 1113-1116).

At least one instance of self-assembly of a metabolized portion of an administered drug compound has been disclosed; however, the resultant appears to be a relatively inactive form which is simply a metabolite of the active drug. Aclacinomycin A, a glycosylated anthrocycline is apparently metabolized first by deglycosylation to obtain 7-deoxyaklavinone which then dimerizes. However, the dimer has no known metabolic or biological activity (Komiyama, T., et al, *J Antibiotics* (1979) 22: 1219-1222; Egorin, M. J., et al, *Cancer Chemother Pharmacol* (1982) 8: 41-46).

The above citations illustrate that inactive materials are available which have been assembled using standard synthetic techniques to obtain active compounds. However, advantage has not been taken of in situ self-assembly and its corresponding desired effect on the dose-response pattern. The process of the invention, in which a biologically active agent is covalently formed in situ from at least two relatively inactive components is thus itself useful and novel, regardless of selectivity.

DISCLOSURE OF THE INVENTION

The invention involves the assembly of two or more portions of a desired end product at the location at which activity is to be exerted. For example, in one embodiment, a cytotoxic substance able to destroy a particular type of target cell is assembled from two components which are individually relatively nontoxic. This process is per se helpful since it permits harmless components to be separately supplied. The process (rather than, necessarily the product) can be selective because the amount of cytotoxic material assembled in the environment of the desired target cell type is greater than the amount of material assembled in the immediate environment of, at the surfaces of, or within, other nontargeted cell types. The target microenvironment may not be represented by a particular cell type, but by an organism, extracellular matrix substance, or mixture, such as an an insect, weed, or toxic waste materials.

There may be one or several reasons for this passive selectively. First, the observed selectivity may merely reflect increased concentrations of the reactant(s) due simply to the attractiveness of the microenvironment for them either as a result of specific binding or of general features such as polarity or fluidity, or both. Second, the microenvironment may preferentially have the ability to activate one or more of the components. Third, the microenvironment may less effectively inactivate one or more reactants, or less effectively retain it. Fourth, the microenvironment may distribute one or more reactants within its own milieu so as to localize a high concentration. All of these factors may raise the effective concentration of one or more reactants. In addition, there may be a positive effect of the microenvironment on the forward rate constant of the synthesis reaction.

The substance having the desired biological activity may be a conjugate of two (or more) different relatively inactive components, or may be a polymeric or oligomeric substance (herein also called a conjugate) formed by monomer condensation. In any event, the reaction which occurs in situ is at least a bimolecular reaction wherein at least two separate, but not necessarily different, externally applied molecules are covalently ligated. The components which become parts of the conjugate may either be the components as supplied, or the resultant of enzymatic or non-enzymatic activation either in situ in the microenvironment or in the progress of the administered substance in reaching the microenvironment. For agrichemicals, activation by sunlight is often significant mechanism; other environmental conditions, such as temperature or relative humidity, may also modify the components as supplied.

Therefore, in one aspect, the invention is directed to a method of modifying a condition responsive to a conjugate, but relatively unresponsive to the individual members of said conjugate, which method comprises administering to the general environment in which the condition is found, the individual components of the conjugate. The components have such characteristics that they will more readily combine to form the desired conjugate at the location of the desired target condition.

In particular, for example, it may be desirable to target certain tissues or cells in an animal subject. In one illustration, the invention is direction to a method of effecting the demise of malignant cells in a vertebrate subject by administering the member of the conjugate to a vertebrate afflicted with the malignancy. In another illustration, the invention method may be used for treating infection in subjects by administering the components of an antibiotic conjugate to them. In still another illustration, the method is directed to destroying certain organisms in a particular environment, such as selectively destroying an agricultural pest by "administering" the components of a conjugate toxic to the pest to a field of crops. The local environment characteristic of the pests is then such that assembly of the toxin is favored. The conjugate may also be benign, and other exemplary embodiments include assembly of materials beneficial to particular crops, such as conjugates conferring insect resistance or a desired hormonal activity in an agricultural context, where the assembly is favored by the environment provided by the crop.

In another aspect, the invention relates to pharmaceutical compositions, agricultural preparations, and other materials useful in performing the foregoing methods.

In still another aspect, the invention relates to the covalent formation of a biologically active agent from at least two relatively inactive components in situ, whether or not the formation is selective with regard to the microenvironment.

BRIEF DESCRIPTIONS OF THE DRAWINGS

FIG. 6 shows the assumed parameters and equations for a computer model of the behavior of the self-assembling active conjugates of the invention.

FIGS. 10a and b compare the selectivity provided by serum-free and nonserum-free environments when the biologically active agent is preassembled or not; FIG. 10a shows the effectiveness of preassembled agent with and without the presence of serum; FIG. 10*b* shows the comparable data when the components are provided.

FIG. 11 shows the results of a temperature selectivity determination using hemolysis as a criterion.

MODES OF CARRYING OUT THE INVENTION

A. Definitions

As used herein, a "target" condition refers to an organism, tissue, cell, or other biologically responsive material which it is desired either to nurture or destroy. "Target" condition may also include non-biological material such as toxic waste, or the mineral content of soil. Candidate target conditions for destruction are, for example, malignant cells, protozoa, bacteria, or viruses which have infected a subject host; insects, worms, plant viruses or other agricultural pests; fibrin or platelets, when it is necessary to destroy blood clots; specific varieties of lymphocytes, when an antiinflammatory agent is needed; fungi which attack plants; or unwanted plants, themselves (weeds). Candidate targets for nurture include bone cells to encourage growth or food crops to encourage early maturity. Other desired effects on a "target" condition may include mutation of a genome, histologic staining, and protection against toxicity. The foregoing list clearly is not exhaustive, but is intended to illustrate the scope of what is meant by "target" condition.

This condition must occur within a general "environment" which includes, of course, other organisms, tissues, cells, or other biologically or generally responsive material. These other "nontarget" conditions are defined as the "surroundings" below.

"Microenvironment" associated with a target condition, such as an organism, tissue, cell, or other target refers to the immediate vicinity thereof wherein the presence of a particular biologically or generally active agent will result in this agent's exerting its desired effect.

For example, with respect to an individual cell, the microenvironment may be at a cell's interior, if the agent exerts its effect in the cytoplasm; or at the nucleus; or it may be at the surface of the cell if the cell is capable of uptake of the agent or if, indeed, the agent acts at the cellular surface; or it may be in the extracellular matrix. With respect to a tissue, "microenvironment" refers to a location proximal to the tissue, such that the tissue is selectively targeted by the biologically active agent if the biologically active agent is present within it. Similarly, with respect to an organism, for example a plant or insect, the microenvironment includes sufficient proximity that the organism is acted upon by the biologically active agent, not necessarily because of the nature of the agent per se, but because of the physical location thereof relative to the organism.

Thus, "microenvironment" is intended to distinguish those locations wherein the biologically or generally active agent must be present in order to affect the target condition. "Microenvironment" thus has a functional definition: it includes those volumes of space wherein the biologically or generally active agent is capable of affecting the target condition as opposed to affecting nontargets.

"Surroundings" refers to any volume of space which is of interest—i.e., included within the "environment"—which does not encompass the microenvironment.

"Biologically active agent" refers to a material which has some impact on the metabolism of target biological material, cells, tissues or organisms. Often, this impact will be that of a toxin where the target cell, tissue, or organism is an undesirable one. Additional examples of targets where toxicity or destructive effect is desired include excess adipose cells, bacteria capable of causing infection, weeds, rodents and other undesirable organisms in the environment. The biologically active agent could, however, be designed to enhance a particular cell or organism at the expense of others. For example, such agents might be useful in supplying nutrients for desired symbiotic bacteria or for enhancing the growth of desired specialized tissues such as helper T cells.

Such agents might also be mutagens or labeling materials, as set forth above.

The nature of the biological activity may also be more subtle. For example, for use in organisms which have an immune system, immunity can be induced against the desired adduct by supplying it conjugated to carrier protein. The assembly of the antigen in the target tissue, if selective for the target tissue, may make these tissues susceptible to the specific immune response previously induced.

Because most of the applications envisioned with respect to the method of the invention involve organisms, tissues or cells as target microenvironments, the term "biologically active" in describing the conjugate has been consistently used. However, it should be recognized that the target microenvironment might also be a non-living entity such as toxic waste material which is responsive to chemical, physical or other activity on the part of the conjugate. Therefore, to make clear that the invention is intended to encompass this extension of the concept into the non-living world, the term "generally active" conjugate or agent has been coined. This is intended to include, for example, the formation of chelators which may be capable of entrapping excess mineral content in soils, or compounds chemically reactive with a toxic waste material, or materials which have a desired leavening effect on soil all in the conjugated but not unconjugated form.

In the context of the present invention the biologically or generally active agent will be a "conjugate". As used herein, "conjugate" refers to a compound which is the covalent product of at least two formerly independent components. The conjugate may be a simple covalently joined pair of individual components that are the same or different, or may be a multimer or polymer of a single component, or of more than one type of individual component. The nature of the conjugate of course depends upon the desired biological or other effect. In any event, the components which form this conjugate must be covalently bound in the process of its formation. (It should also be noted that the biologically or generally active conjugate may not be the immediate product of an initial covalent bond formation between the individual component molecules, but may represent further conversion of the adduct.)

The individual components used in the formation of the conjugate do not have the biological or other activity of the conjugate itself. Of course, these components may have some residual minor biological or analogous activity, but are clearly not "active" ingredients in the sense that the conjugate must be.

B. General Description

The invention resides in the covalent formation of a biologically or generally active conjugate in situ. A variety of reaction types may be employed, including various condensation reactions of carbonyl (aldehyde or ketone) moieties with amine related groups such as hydrazine or O-substituted hydroxylamine; metal bis and oligo chelation, photodimerization, Diels-Alder condensation, silyl ether formation from silanol, addition polymerization, and so forth.

Photo-induced polymerization may be particularly appropriate to agricultural applications, since the desired agricultural agent will self-assemble preferentially in the presence of sunlight. For example, the compound

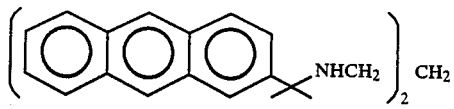

polymerizes in the presence of light to form an amphipathic polycationic polymer.

The formation of a conjugate in situ is particularly advantageous when such formation is favored at a particular microenvironment target location. The reasons for this preference may be several fold:

COMPONENT CONCENTRATION ENHANCEMENT; AMPLIFICATION OF SELECTIVITY

The microenvironment may be such that the components which are reactive to form the desired conjugate are selectively concentrated into a smaller volume than that in which they find themselves generally in the surroundings. Because the rate of multimolecular reactions depends on the concentrations of the individual components, this enhancement of concentrations may impact the rate of formation of the conjugate with amplified effect. For example, if the conjugate A-B is to be formed by the joinder of its individual components, and the reaction is truly bimolecular (i.e., the rate is directly proportional to the concentrations of both A and B), doubling the concentration of A and doubling the concentration of B in the microenvironment results in a four-fold increase in the concentration of conjugate as compared to the surroundings where the concentrations are not doubled, at least during the time frame wherein the concentration of A-B is dependent on the bimolecular reaction. This amplification of selectivity is directly due to the bimolecular nature of the reaction.

Similarly, if the conjugate is formed by the reaction:

$$xA \rightarrow A_x$$

depending on the mechanism of the reaction, the rate may most simply be dependent on the concentration of A to the zero, first, second, or x power. Therefore, in all cases except where the rate is dependent on $[A]^\circ$ or [A], such amplification is also available.

The preferential concentration of one or more components which make up the conjugation reaction in a particular microenvironment may be due to a number of factors. First, peculiarities of the microenvironment that are attractive to the reaction component, such as its fluidity, polarity, hydrophobicity, surface charge, pH, and so forth may result in a significant concentration enhancement. Second, a higher concentration may also be due to a specific interaction between an indigenous material and one or more of the components of the desired reaction. For example, the presence of DNA on the surface of cancer cells or their anionic membranes result in a selective binding of certain substances, which are thereby made available in higher concentration to react with the other member of the conjugate.

Alternatively, an indigenous material may selectively inactivate one of the components of the reaction forming the conjugate, as appears to be the case with regard to serum in the formation of toxic conjugates. In this case, the *absence* of serum in the target environment serves to enhance the rate of the formation of the conjugate in the target as compared to the surroundings which contain higher concentrations of serum.

Third, the component may require activation in order to participate in the reaction. Thus another factor influencing the formation of biologically active ingredients is the possibility of activating one or more of the components participating in the conjugation reaction at the desired location. For example, if one of the reactants is present in a protected form, cleavage of the protecting agent frees this component for reaction. To the extent that this activation is preferred in the desired microenvironment, the formation of conjugate is enhanced.

Fourth, the nature of the surroundings may inactivate one or more of the reactants, while they are less subject to inactivation at the target microenvironment. This, too, results in an effectively higher concentration at the target.

All of the foregoing factors are amplified by virtue of the participation of these components in a multimolecular reaction, provided the rate of the reaction is dependent on concentration factors collectively greater than the first power of a single component.

RATE CONSTANT DIFFERENTIALS

The second factor affecting the in situ production of the biologically active agent is the impact of the microenvironment on the rate constant of the conjugation reaction. It is well known that the course of chemical reactions in general is regulated by the nature of the medium in which they take place. Factors such as presence or absence of detergents, the presence or absence of protons, and the magnitude of the dielectric constant can be significant in determining the value of the rate constant. Therefore, it would be expected, for example, that reactions which are speeded by higher pH values would preferentially occur at microenvironment locations where the medium is more basic than that of the surroundings.

The effects can be quite dramatic; for the conjugation reaction between decanal and "AOG", illustrated below, the presence of, a change in the nature of, a detergent varies the rate constant by a factor of 10.

Closely related to the influence of the environment on the rate constant per se is the effect of temperature on reaction rate. While not formally a part of the rate constant, an increase in temperature always accelerates the progress of a reaction to equilibrium. Accordingly, the self-assembling biologically active agents of the invention are automatically selective for high temperature environments. Advantage can be taken of this selectivity if an effect on higher temperature targets is desired at the expense of environments whose temperature is lowered.

There will be some temperature selectivity inherent in the reactions involving the biologically active agent and the target in any event. This is reflected in the effective temperature on these reactions per se, and on the stability of the reactants involved.

A direct confirmation of the selectivity conferred by self-assembly is shown in Example 7 below.

INTRINSIC SELECTIVITY

The impact of the foregoing selectivity factors on the effectiveness of the treatment is automatically made more selective by the fact that the biologically active agent is the result of a cooperative effect of separate components. The necessity for two or more materials to react cooperatively in order to achieve a biological effect is well known to result in a steeper dose-response curve than would have been obtained by using a single agent acting alone. A measure of this cooperative effect is the "Hill constant", which increases as the cooperative effect becomes more important. This concept is discussed, for example, in Lehninger, *General Biochemistry*, 751-753. The derivation of the Hill equation is shown in Cantor, C. R., et al, *Biophysical Chemistry*, Part 3 (1971), W. M. Freeman, San Francisco, pp. 862-866.

Figure 1:
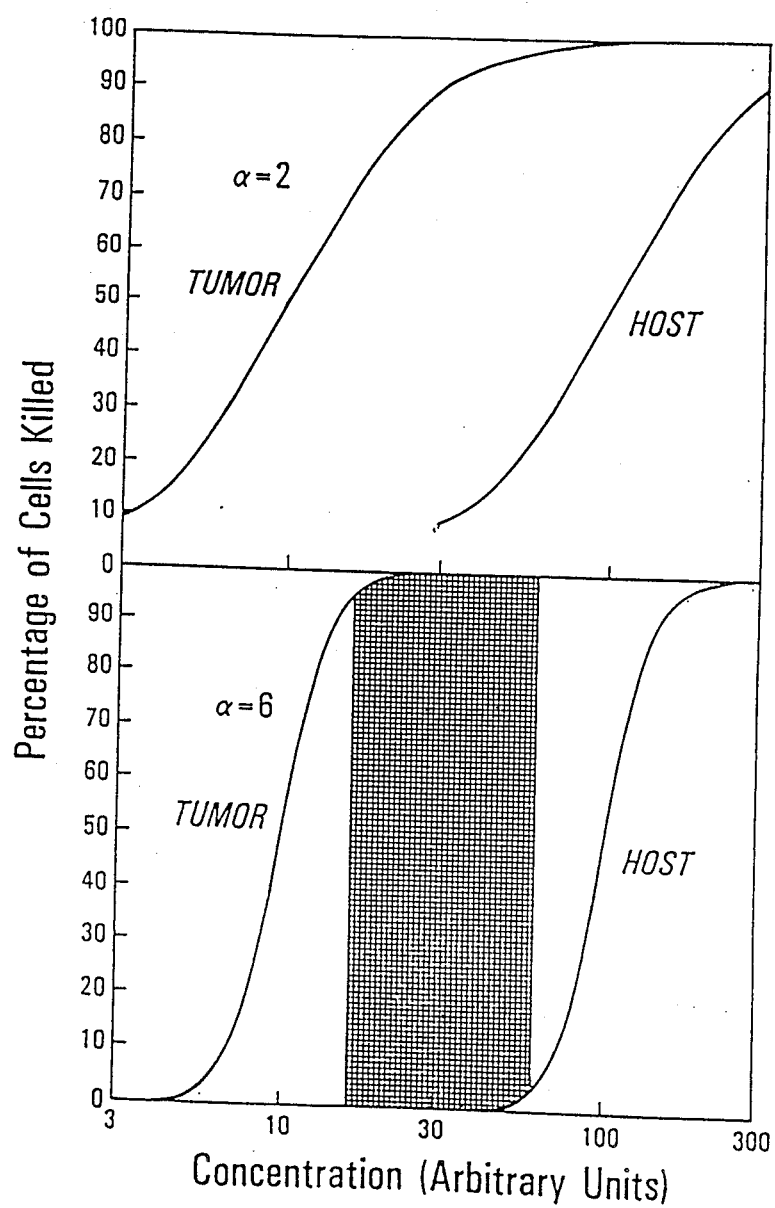
FIG. 1 shows a comparison of hypothetical dose response curves having different Hill constants.

FIG. 1 shows a generalized graphic representation of the influence of the value of the Hill constant, or cooperative activity, on the steepness of the dose-response curve, and the resultant influence of the Hill constant on the therapeutic window for materials having comparable selective effectiveness. For the hypothetical biologically active agent shown in FIG. 1, an $ED_{50}$ for target cells tenfold less than that for nontarget host cells is postulated. For a low value of the Hill constant, $\alpha=2$, intermediate concentrations show measurable effects on both host and target cells. However, at a higher value for the Hill constant, $\alpha=6$, as would be obtained if assembly of the biological reagent were required, an appreciable range of concentrations exists wherein the target cells are highly effected but the host cells are relatively unscathed.

This results, of course, from the steeper dose-response curves that are obtained when assembly is required. The ability to discriminate target and nontarget may also be enhanced by the effect of competition between assembly rate and clearance rate of the components, so that nontarget environments may deactivate or clear the reactants before they can be assembled to any detectable concentration of conjugate. A classic example of this effect is described by Chan, V., et al, in "Calmodulin and Intracellular $Ca^{+2}$ Receptors" (1982) Plenum Press, New York, pp. 199-217. In this naturally occurring model, the allosteric form of a phosphodiesterase requires calmodulin for activation, which calmodulin must be bound to at least two, and most probably four calcium ions. The shallow dose-response curve obtained in response to preformed tetracalcium calmodulin can be made considerably steeper by introducing the complex in five pieces, which must then self-assemble in order to be effective. The activation of the phosphodiesterase is therefore extremely sensitive to calcium ion concentration.

DOSAGE ENHANCEMENT

In some instances, use of the self-assembling materials of the invention results in the ability to administer higher levels of the desired biologically active agent. This result is achieved when the component members of the agent have higher solubility than the agent itself. For example pyridine-2-carboxaldehyde and 2-hydrazino pyridine have been shown to form supersaturated solutions of the product hydrazone.

FORMULATION AND ADMINISTRATION

The components of the biologically active agent to be assembled in situ can be administered in a manner suitable to the environment to be addressed. If to be administered as pharmaceuticals, the relevant components may be administered separately or together in conventional formations using either localized or systemic administration depending on the target cells. For example, it may be convenient to administer the components to a localized condition such as a tumor or localized infection at the intended site of activity since the assembly of the biologically active material will be enhanced by the immediately high local concentrations of the components. Diffusion of the components away from the target site will automatically diminish their tendency to combine to form the biologically active agent.

Generally known methods for administration of pharmaceuticals may be employed, including sustained release matrices, conventional excipients, and simple solutions.

For use as, for example, a pesticide, the materials can be sprayed over the affected area or if in connection with specific crops or forestation, worked into the soil. For use as insecticide, the ingredients may be placed in traps or, if volatile, dispensed from a network of dispensing stations.

Since the biologically active material is being administered essentially in parts, more variation in protocols is possible. For example, if A and B are the components which form the desired adduct A-B, A and B could be administered simultaneously, but at different locations in the environment, depending on the capacity of the surroundings to mix the ingredients. In the case of an organism, for example, A and B could be injected into different muscles; for a field environment, A could be placed in the soil and B in the irrigation system. In addition, different times of administration could be used, thus permitting A, for example, to penetrate the soil, while B is sprayed later, or wherein A is permitted to accumulate in the liver and B later administered.

The amounts of materials to be used and their precise formulation is highly dependent, of course, on the particular ingredient selected and on the condition targeted. Conventional means known in the art for single biologically active materials not assembled in situ are applicable to administration of the individual components, and the invention herein lies not in the specific mode of administration, but rather in the selection of these self-assembling components to provide biologically active agents in situ.

C. Preferred Embodiments

The general approach which constitutes the invention admits a large number of actual embodiments. Advantage can be taken of any known microenvironmental differences, such as those set forth in the Background section herein. Particular preferred embodiments which take advantage of these and other microenvironmental differences are set forth below.

TYPICAL BIOLOGICALLY ACTIVE AGENTS AND THEIR COMPONENTS

A starting point is a consideration of the variety of embodiments available simply with respect to the choice of individual components which will form the covalently bonded conjugate. Listed hereafter are preferred embodiments of the conjugation reactions per se. Candidates for such individual portions of materials with biological activity are multitudinous; the specific illustrations below are merely representative.

In general, in addition to the conjugation of two different moieties to obtain a new conjugate: i.e., $$A+B \rightarrow A-B,$$

a polymerization of A may be utilized, starting with the monomer, or the monomer may be preoligomerized to obtain a larger cytotoxic or otherwise biologically active material in the general reactions, for example:

$$16A \rightarrow A_{16},$$

$$8A_2 \rightarrow A_{16},$$

$$4A_4 \rightarrow A_{16},$$

or $$2A_8 \rightarrow A_{16}.$$

In addition, mixed polymers can be formed from bifunctional or other multifunctional monomers in the typical reactions:

$$4A+4B \rightarrow ABABABAB,$$

or $$4AB \rightarrow ABABABAB.$$

More specifically, in one preferred group of embodiments, self-assembling cytotoxins (SAC) are formed from nontoxic entities. For example, compounds which are known to react under laboratory conditions can be supplied separately and will conjugate in situ to form toxins by simple reaction. One group exemplary of such reactions is that which employs the reaction of hydrazines (or their analogous functional groups such as hydroxylamines, semicarbazides or other amine derivatives) and carbonyls (aldehydes and ketones) to form hydrazones (or the corresponding products, e.g., oximes or semicarbazones) with loss of water as shown below. As is generally understood in the art, the carbonyl moiety may be substituted for, in the foregoing reaction types, by imines and eneamines, wherein rather than the elimination of water, an amine is lost upon reaction with the other, hydrazine-type reagent.

The effectiveness of the cytotoxicity of the products is enhanced if the individual components are bifunctional and are thereby capable of forming polymers.

CHD+DAPG

In one reaction of this type, cyclohexane-1,4-dione (CHD) is reacted with 1,2-diamino-3-phenyl guanididium iodide (DAPG) to form multimeric hydrazones as shown in Reaction Scheme 1:

Reaction Scheme 1

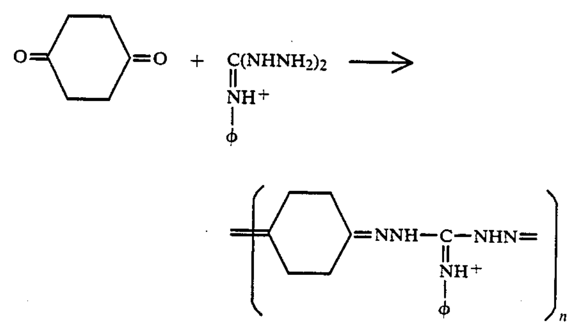

The putative product shown in Reaction Scheme 1 is evidently cytotoxic, since a suspension of human erythrocytes in a solution containing both CHD and DAPG in phosphate buffered saline is 95% lysed or aggregated within 1-14 hours under physiological conditions (the precise time depending on the concentrations) whereas erythrocytes are stable for at least 24 hours in plain PBS, and also in solutions containing either DAPG or CHD alone. In addition, when erythrocytes are incubated with mixtures of CHD and DAPG, a substantial induction period is observed during which no lysis or aggregation occurs, due to the time lag in formation of the cytotoxic material. Whether lysis or aggregation results depends on relative concentrations; excess CHD results in lysis, equimolar concentrations in aggregation. The cytotoxicity may be due to the formation of the polycation, analogous to the known antitumor activity of poly-(L-lysine); Arnold, L. J. *Proc. Natl Acad Sci* (supra).

DECANAL AND AOG

Another combination using this same functionality employs decanal and N-amino-N'-1-octyl guanidine (AOG). The condensation of these two components is shown in Reaction Scheme 2:

Reaction Scheme 2

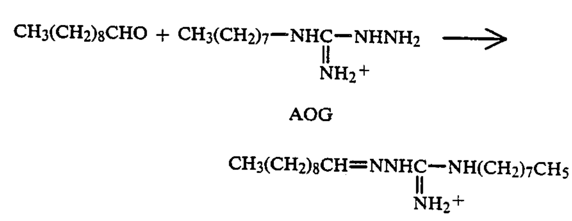

The components react as shown to form the more cytotoxic hydrazone N-1-decylidenimino-N'-octyl-guanidine (DIOG). The cytotoxicity of this reaction mixture was also shown in a suspension of human erythrocytes, as well as in bacteria, yeast, and HeLa cells.

The cytotoxicity of DIOG is thought to be due to the interaction between the cationic proteinated form and the biomembranes (Murdoch, K. C., et al, *J Med Chem* (1982) 25: 505-518).

POLYMERIC HYDRAZONES

A somewhat more elaborate variation of this reaction is shown in Reaction Scheme 3:

Reaction Scheme 3 nonylCONHCH$_2$CH$_2$NH(CH$_2$CH$_2$NHCOCH$_2$CH$_2$CCH$_3$)$_2$ or —NH$^+$
(with =O and diketone structure)

+ nonylCONHCH$_2$CH$_2$NH(CH$_2$CH$_2$NHCOCH$_2$CH$_2$C or —NH$^+$
‖
N
|
NH
|
C=NH$_2$$^+$
|
NH
|
NH$_2$

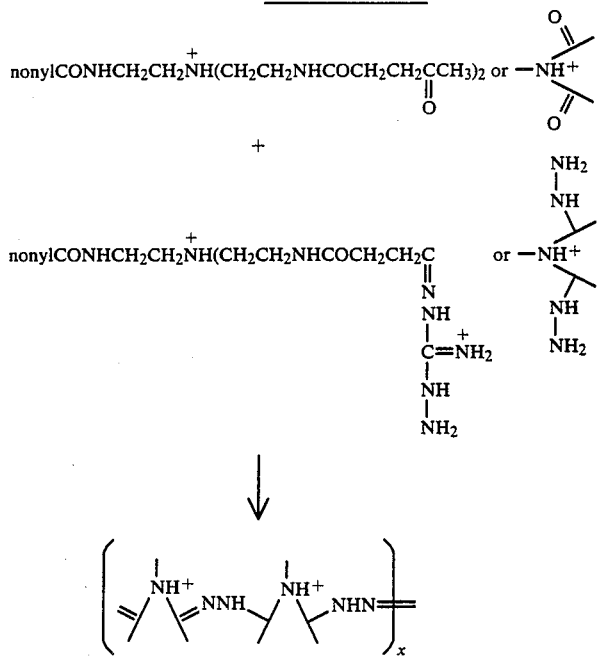

The reagents for Reaction Scheme 3 are prepared by reacting decanoyl chloride with tris(2-amino ethyl) amine, followed by reaction of the remaining free amino groups with the succinimidyl ester of acetylpropionic acid as shown in Reaction Scheme 4, to obtain the diketone. The diketone is then reacted with diaminoguanidine to obtain the corresponding reactive dihydrazine.

Reaction Scheme 4 nonylCOCl + N(CH$_2$CH$_2$)NH$_2$)$_3$ ⟶ nonylCONH$_2$CH$_2$CH$_2$N(CH$_2$CH$_2$NH$_2$)$_2$

↓ 2 CH$_3$COCH$_2$CH$_2$COONS

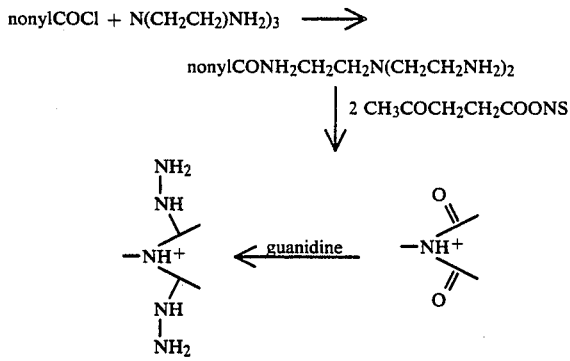

The polymeric compound prepared in Reaction Scheme 3 is expected to be cytotoxic since amphiphilic citronic polymers in general are more tightly bound to membranes than the corresponding monomers and can disrupt membrane bound enzyme activity, cell division, and membrane transport. This particular cytotoxic polymerization may occur more easily on neoplastic cell surfaces since the microenvironment is more favorable.

The polymer prepared in Reaction Scheme 3 can be demonstrated to be disruptive to membrane vesicles by preparing purified egg lecithin vesicles with 230 Å diameters according to the method of Batzri, S., et al, Biochim Biophys Acta (1973) 298: 1015. The vesicles are treated with mixtures of the monomers in the range of $10^{-6}$–$10^{-2}$M using a phospholipid concentration of $10^{-4}$M. Controls are performed using each monomer alone in the same concentration range. At intervals, aliquots of the reaction mixture are quenched with an excess of a monoketone, denatured with urea, and cleared of phospholipid by anion exchange chromatography.

A convenient ketone for quenching the reaction is acetopropionamide. The total hydrazone concentration is then estimated using ultraviolet absorption and the polymer size distribution is estimated using gel exclusion chromatography. Lysis, fusion and/or aggregation of vesicles is followed semiquantitatively as a function of time by observing the associated increase in light scattering (Portas, A., et al, Biochemistry (1979) 18: 780-790) and vesicle lysis can be estimated quantitatively according to the leakage of the fluorescent dye 6-carboxyfluorescein by the method of Gad, A. E., et al, Biochim Biophys Acta (1982) 690: 124-132.

The relatively low surface viscosity and high surface negative charge (Arnold, L. R., et al (supra)) characteristic of at least some neoplastic cell surfaces encourages the selective copolymerization of the ionic ketone with a cationic dihydrazine as shown above.

Reaction Scheme 5 shows the formation of a polymer whose toxicity is due to its ability to polyalkylate the materials in its immediate environment. The polymeric product is a result of condensation of the alkylating fragment shown as formula "ALK" in reaction scheme 5 with a dialdehyde or diketone, thus resulting in a molecule which is capable of causing a multiplicity of the toxic alkylation reactions. It has been shown that the starting material of formula "ALK" is specifically taken up by tumor cells due to the lower pH levels in the tumor as opposed to normal extracellular matrix (Bramhall, J., Biochemistry (1986) 25: 2958-3962; Denny, W. A., et al, J Med Chem (1986) 29: 879-887). Due to this tumor cell specificity, the concentration of the toxic polymer will be higher in the target tumor cells than in the surrounding tissue.

Reaction Scheme 5

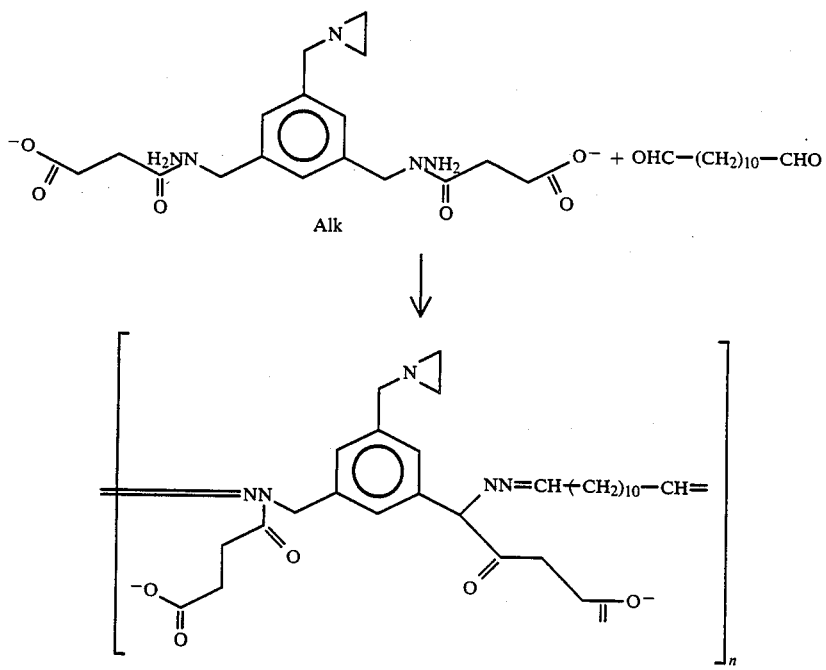

An additional exemplary polymer which is toxic by virtue of its polychelation properties is formed by the in situ reaction of a porphyrin, for example, tetrakis(4-carboxyphenyl) porphyrin with a dialdehyde such as, for example,

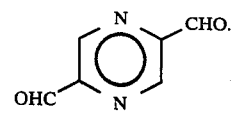

The porphyrin, of the formula should accumulate selectively in solid tumor tissue in a manner analogous to hematoporphyrin and is capable of forming the polychelating polymer by reaction of the side chain semi-carbazide moieties of the dialdehyde or diketone.

OTHER CARBONYL DERIVATIVES

A wide variety of carbonyl and dicarbonyl compounds, as well as hydrazine and dihydrazine compounds are available for self-assembling cytolytic toxins. Additional carbonyl-containing compounds include cyclohexanone, daunorubicin, streptomycin, cortisone,

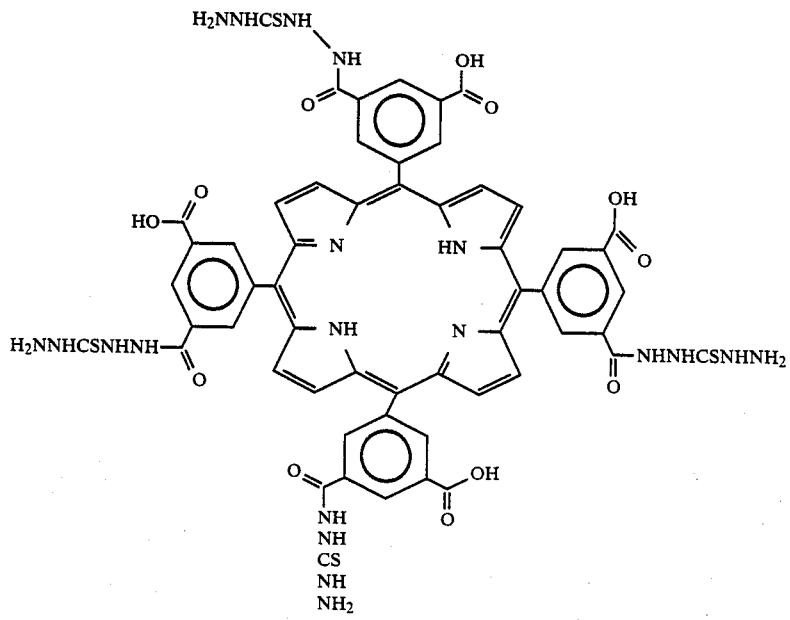

2-methyl cyclohexanone, cycloheptanone, CH₃(CH₂)₃COCOCH₃, benzaldehyde, cyclopentanone, heptanal, hexanal, and pyridine-2-carboxaldehyde. Additional hydrazines or hydrazides include hydralazine, which is an antihypertensive, isoniazid (a semicarbazide), which is an antitubercular, phenylhydrazine, and phenylsemicarbazide. Inclusion of a biologically active component in a polymer may render it more effective by increasing clearance time. The addition products of carbonyls and hydrazine, such as bisantrene (antitumor), and robenidine (antiprotozoan) also have known biological activities.

Additional types of carbonyl derivatives include the formation of O-substituted oximes from O-substituted hydroxylamines (Young, P. R., et al, *J. Am Chem Soc* (1975) 97: 6544–6551; Jencks, W. P., *J Am Chem Soc* (1959) 81: 475–481; Conant, J. B., et al, *J Am Chem Soc* (1932) 54: 2881–2899; Rideout, D., *Science* (1986) 233: 561–563), and the rate constants for these reactions under physiological conditions are favorable.

There is an extensive literature describing compounds with known toxicity or other biological activity which greatly exceeds that of their individual components. See, for example, descriptions of the comparative cytotoxicity of melitin-II, which is more than two orders of magnitude greater than the activity of either of the individual peptides which compose it (Schroeder, E., et al, *Experientia* (1981) 27: 764–765). Hydrazones with antitumor activity which are formed from relatively nontoxic keto and hydrazino portions (Hirayama, T., et al, *Yakugaku Zasshi* (1980) 100: 12225–1234; Korytuyk, W., et al., *J Med Chem* (1977) 20: 745–749; Renfrew, R. W., et al, *Aust J Chem* (1980) 33: 45–55; Springarn, N. E., et al, *J Med Chem* (1979) 22: 1314–1316). In addition, bis alkylating agents show greater antitumor activity than monoalkylating agents (John, K. W., et al, in Molecular Aspects of Anticancer Drug Action, Neidel, S., ed., Verlag Chemie (1983), Basel, pp. 315–361), and bis-acridinylamines are cytotoxic, although 9-aminoacridine is not (Denny, W. A., et al, *J. Med Chem* (1985) 28: 1568–1574).

Other reaction mechanisms can be used to form biologically active agents and are also illustrative of the invention. Self-assembling polychelators using nitro-substituted benzyl to confer selectivity for hypoxic tumor cells, or using rhodamine moieties selective for carcinoma cells are exemplified by the reduction of derivatized hydroxylamine esters to obtain the chelating group,

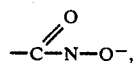

wherein the presence of naturally occurring iron ion drives the assembly. (Abnormally high iron levels are observed in some leukemias.)

Polysiloxanes are obtained using organosilane monomers derivatized to cell-specific reagents such as rhodamine; an important intermediate is, for example,

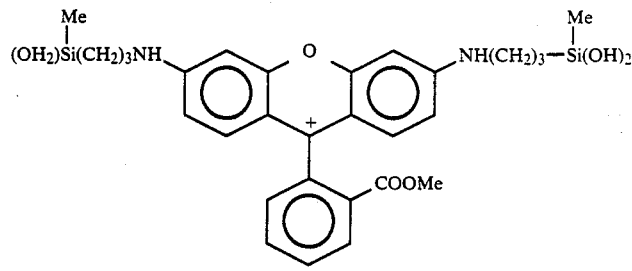

Polymerization of the side chains leads to the formation of the toxic polymers.

Thermal cycloadditions based on the Diels-Alder condensation of 1,3-dienes with an isolated double bond can also be used, for example to polymerize:

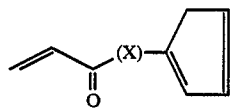

wherein X can be a specificity-conferring moiety which may include, for example the nucleic acid-specific moiety,

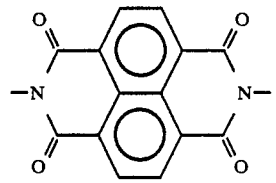

or a polyflourinated hydrocarbon. Indeed, the isolated double bond might be formed in situ from a 3-oxoalkyl trialkylammonium substituent.

The resulting polymer is of the formula

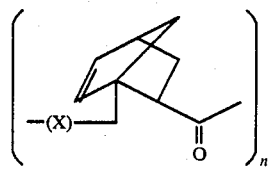

Polymerization may also be based on the reaction

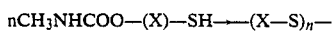

wherein X, again, may contain any desired groups conferring selectivity; or by the reaction

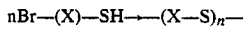

The thiol could, in either case, be produced in situ be reduction of a disulfide bond or similar group.

Thus, the invention is directed not to specific combinations of relatively inactive biological components which are capable of generating biologically active materials per se, but rather to the use of this assembly in vivo to obtain advantages in drug administration, including selective amplification of the effect of the assembled biologically active material.

MODIFICATIONS TO PERMIT SELECTIVE CONCENTRATION IN THE MICROENVIRONMENT

To confer selectivity on the foregoing conjugation reactions, one approach employs linking the components to a moiety attracted to the target microenvironment if the components themselves are not intrinsically so attracted. For example, advantage may be taken of the known affinity of an apoAI protein analog which binds specifically to vesicles containing cholesterol as described by Fukushima, D., et al, *J Amer Chem Soc* (1981) 3703–3704. A tendency to home to cholesterol ceels or vesicles can be conferred by modifying the reagents so that this peptide replaces the nonyl residue in, for example, the diketone component of Reaction Scheme 3 above.

In this embodiment, the peptide of the formula: Pro-Lys-Leu-Glu-Glu-Leu-Lys-Glu-Lys-Leu-Lys-Leu-Leu-Leu-Glu-Lys-Leu-Lys-Glu-Lys-Leu-Ala, designated "ApoA" herein, is protected and attached by its carboxyl terminus to a solid support according to the general procedure of Merrifield, et al. The protected peptide bound to solid support is then treated with succinic anhydride and the resulting monoamide reacted with the tris(2-aminoethyl) amine to form a compound of the formula:

$$(H_2NCH_2CH_2)_2NCH_2CH_2NHCOCH_2CH_2CON\text{-}H\text{—}ApoA.$$

This intermediate can then be reacted with acetyl propionyl chloride to obtain the diketone analogous to that shown in Reaction Scheme 3, above but bearing the cholesterol affinity peptide, ApoA.

The diketone, which is now preferentially concentrated in the microenvironment of cells that have significant cholesterol content at their surfaces, can be used for conjugation in situ with the hydrazine derivative shown in Reaction Scheme 3 exactly as shown, or with the analogous hydrazine derivative also containing the ApoA, or with any other hydrazine derivative such as DAPG. In any of these cases the polymerization should occur more rapidly on cholesterol-laden vesicles and cells.

Conversely the preference of the ApoA for cholesterol-laden vesicles could effectively be used to inhibit polymerization in this microenvironment by using as a terminator of polymerization, a monoketone containing the ApoA peptide. An appropriate monoketone is prepared by direct reaction of acetyl propionyl chloride with the protected ApoA peptide derivatized to solid support. The polymer forming reagents can be any compounds having dicarbonyl and dihydrazine or related type functionality. Since the monoketone will be attracted more to the cells containing high concentrations of cholesterol, the polymerization will be more effectively terminated at these locations.

One or both of the components of the reaction designed to form cytotoxic hydrazones or analogous conjugates may also be derivatized to materials known to bind preferentially to tumor cells. Among such materials are rodamine 123, hematoporphyrin derivative, and sulphamethazole. (See, for example, Johnson, L. V., et al, *J. Cell Biol* (1981) 88: 526–535, which discloses a variety of cationic dyes which exhibit mitochondria-specific binding.) Other materials known to bind preferentially to certain cellular membranes include amphotericin B, which is an ergosterol-specific antifungal, and colistin, which is a phosphatidyl ethanolamine-specific antibacterial agent.

Rhodamine bound to a silyl monomer containing an alkylating agent side chain can, for example, be used to transport and selectively concentrate this monomer in tumor cells where it then polymerizes. Thus, a compound of the formula can be derivatized to rhodamine through one of the hydroxyl groups in order to confer specificity to tumors. Upon release by hydrolysis in vivo, the monomer polymerized to the polymer of the formula which contains multiple alkylating moieties and thus forms a toxic polyalkylating agent.

MODIFICATIONS TO PERMIT SELECTIVE ACTIVATION IN THE MICROENVIRONMENT

Additional embodiments include employment of materials which are activated selectively at the surface of particular cells. These include, for example, compounds having the side chain peptide D-Val-Leu-Lys-NH which is cleaved by plasmin (Carl, P. L., et al., (supra)). Reaction components protected by this side chain, such as or are preferentially activated at surfaces of the cells having high plasmin concentrations; transformed cells are among those which do. Thus, polymerization with a dicarbonyl-containing compound also preferentially occurs at transformed cells. Polycationic compounds can also be formed from monomers activated in this way. For example, $$\text{D-Val—Leu—Lys—NHNHCNH(CH}_2)_{10}\text{CHO} \atop \text{NH}_2^+$$

polymerizes upon deprotection in the plasmin-rich environment of transformed cells to form a cytotoxic, amphiphilic polycation similar to polylysine or melletin.

Additional protecting groups which can be activated selectively by deprotection at particular types of cells include the substrates for γ-glutamyl transpeptidase, which is found in high concentration in certain tumors; peptide sequences specifically reactive with proteases used by insects in order to digest plants; or to proteases involved in pathogenicity of fungal plant diseases. All of these groups can be used as protective groups selectively activated in particular microenvironments.

In, perhaps, a more subtle embodiment wherein the targeted microenvironment exhibits selective activation (or less deactivation) lie in the ability of serum to incapacitate both a biologically active conjugate and one or more of its components. Tumor cells are known to have low concentrations of serum as compared to normal tissues, probably due to the high percentage of dead cells and to poor vascularization (Bohmer, R. M., et al, *Cancer Res* (1985) 45: 5328-5334). Therefore, drugs which selectively kill cells in low serum environments exhibit tumor selectivity, presumably because the tumor cells contain insufficient serum to inactivate these agents. It is demonstrated in the examples below that not only are conjugates such as DIOG which result from individual components which form known cytotoxins (dodecanedial or decanal and AOG) less toxic to cells in the presence of large amounts of serum, this differential is exhibited more dramatically when the toxin is self-assembled than when the finished toxin is supplied. Therefore, apparently, the serum not only partially inactivates the cytotoxic product, but inhibits, in some manner, the formation of this product. The environment which is associated with the target cells, characterized by a low serum level, is therefore more activating—i.e., actually less deactivating, than the surrounding environment of normal tissue. In this instance, it is unnecessary deliberately to modify the components to confer selectivity in their effective concentration in the desired microenvironment. The microenvironment itself provides the needed selectivity with respect to "activating" or not deactivating the components per se.

MODIFICATIONS TO PERMIT SELECTIVE STABILITY IN THE MICROENVIRONMENT

Another approach to effecting an increased concentration takes advantage of the relative stability of components to particular cellular conditions. For example, since tumor cells are known to have low esterase activity monomers having central ester linkages would have higher effective concentration in such environments in comparison to environments where they undergo degradation.

In addition, the precursors may have enhanced permeability to the target cell or target conditions, as compared to the product which has the biological activity. Thus, although the biologically active agent may be actually ineffective when supplied presynthesized due to such permeability problems, the combination of the precursors permits in situ formation of the biologically active material. This may be verified by microinjecting the product directly into a target cell or otherwise penetrating barriers to its permeability in reaching the desired microenvironment and showing greater toxicity than either component injected alone.

Similarly, this localized self-assembly may be verified by using labeled product and labeled components in the above determination and comparing the depletion of levels of label in the desired target area. The rate of loss of label from the target would be lower for the conjugate, and for the combination of both components supplied together, than for either of the two components supplied alone, if self-assembly occurred in situ in the target environment.

SELECTIVITY BY EFFECT OF THE MICROENVIRONMENT ON REACTION RATE

Rate constants are generally affected by the properties of the milieu in which a reaction takes place. Many rate constants are, for example, affected by the pH of the immediate environment. The second order rate constant for hydrazone and similar derivative formations are particularly thus sensitive; the second order rate constant for furfural semicarbazone formation at pH 6.5 is 10 times larger than the corresponding value at pH 7.5, and this formation is thus favored in low pH environments. Tumor cells, in particular, contain abnormally low pH environments because of metabolic differences.

Another factor which dramatically affects rate constants is the polarity of the solvent, and thus the lipid content of the microenvironment will have a considerable impact. The reaction rate for decanal and N-amino-N'-1-octylguanidine varies by at least a factor of 14 with respect to the surfactant content of the environment. The rate of reaction between nickel dication and pyridine-2-azo-p-dimethylamine is also sensitive to the concentration of anionic surfactants.

COMPUTER MODELLING OF SELF-ASSEMBLY

A mathematical model showing the kinetics of self-assembly in the human body for target as compared to normal tissue has been devised. The model envisions three compartments as shown in FIG. 6. The model assumes that individual components A and B will assemble in situ to form the cytotoxic component C. The forward rate constant is assumed to be the same for all of tumor tissue, normal tissue, and in serum. The relative sizes of the normal tissue, tumor tissue, and serum "compartments" are roughly as shown in the figure, wherein the bulk of the volume is occupied by normal tissue, somewhat less by serum, and considerably less by tumor.

A and B are administered to the subject by intravenous injection, thus appearing initially in the serum. They are lost from the serum by normal clearance procedures and interchange with the normal and tumor compartments with the rate constants there shown. An initial concentration of materials which are not supplied or not present without intermediation or exchange is assumed to be $10^{-10}$ moles per liter in order to avoid division by 0. The differential equations which describe the model are also shown in FIG. 6.

Figure 7:
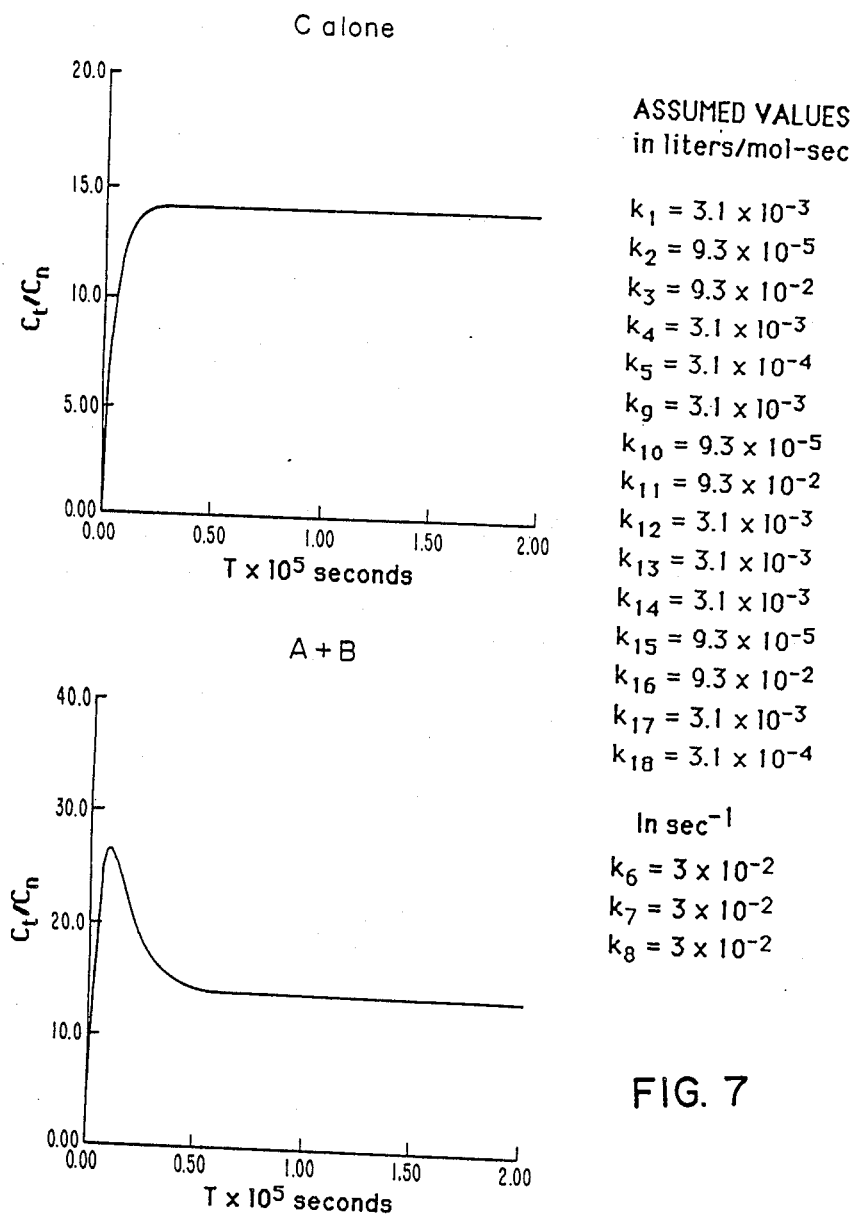
FIG. 7 shows the assumed values for and results of the model of FIG. 6.

The assumptions associated with an initial model are as follows: The relative volume of tumor to normal tissue is assumed to be $10^{-3}$, and of normal tissue to serum, 3. Thus tumor volume is thus 1,000 fold smaller than the total volume of normal tissue. Values for the various rate constants are assumed as shown in FIG. 7. The total drug represented by A, B and C in serum, tumor, normal tissue and excreta is assumed to remain constant, making appropriate correction for the reaction of $A+B\rightarrow C$. The total drug in serum is used to obtain the half-life of the drug in serum, which is assumed to be 4 hours, based on that of methotrexate which is known to be about 2 hours (J. Pharm Sci (1971) 60: 1128-1131). The rate constants ($k_1$-$k_{18}$) shown in FIG. 7 are adjusted to result in this half-life. The rates of membrane penetration for C are treated as identical to those for A and B.

B is treated as non-tumor selective in the choice of the rate constants of FIG. 7, A and C are treated as tumor selective with a selectivity ratio of 10. This ratio is based on that for rhodamine 123 and for EDKC (Nadakawakaren, K. K., et al, Cancer Res (1985) 45: 6093-6094; Bernal, S. D., et al, Science (1983) 222: 169-172; Oseroff, A. R., et al, Proc Natl Acad Sci USA (1986) 83: 9729-9733). Thus, $k_{10}V_s/V_t = k_{13} = k_{11}V_s/V_n$; $k_2V_s/V_t = k_3V_s/V_n = k_4$; $k_5 = k_4/10$; $k_{15}V_s/V_t = k_{16}V_s/V_n = k_{17}$; $k_{18} = k_{17}/10$.

Based on the differential equations and the values of the various rate constants shown in FIG. 7, time dependent concentration plots were obtained for cases wherein C was supplied alone, and wherein a combination of $A+B$ was supplied, the initial individual concentrations being assumed at the level of $5\times 10^{-4}$ moles/l. The results obtained showed that if C were supplied alone, the ratio of the amount of C in tumor to normal tissue rises quickly to a value of about 14 and remains at that level. However, when A and B are supplied together and the concentration of C in tumors is compared to normal tissues, a ratio of concentrations of approximately 26 is obtained quickly, though it then decays, but only to about 14. These results are summarized in FIG. 7.

Thus, modelling systems show that by virtue of the self-assembly characteristics of the method of the invention, the target microenvironment specificity is considerably enhanced.

EXAMPLES

The following examples are intended to illustrate but not to limit the invention.

EXAMPLE 1

Formation of Chelators

Yeast

Pyridine-2-carboxaldehyde (PC) and 2-hydrazinopyridine (HP) are each alone nontoxic to S. cerevisiae YP52 yeast at concentrations below 2 mM when provided over 20 hours at 30° C. in YPD medium in a roller drum. However, when supplied together, these compounds are capable of inhibiting the growth of S. cerevisiae YP52 at 30° C. in YPD. When placed together in the medium at concentrations of 1 mM+1 mM and at 0.5 mM+0.5 mM, substantial inhibition occurs. The adduct, pyridino-2-carboxaldehyde (2-pyridyl hydrazone) (PCPH) of the formula:

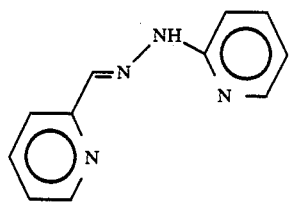

is a chelator and has a structural similarity to 2,2': 6',2" terpyridine which is a known cytotoxin (McFadyen et al, J Med Chem (1985) 28: 1113-1116). The second order rate constant for this reaction is 2 l/mol-sec at 37° C., pH6, in phosphate-buffered saline.

Figure 8:
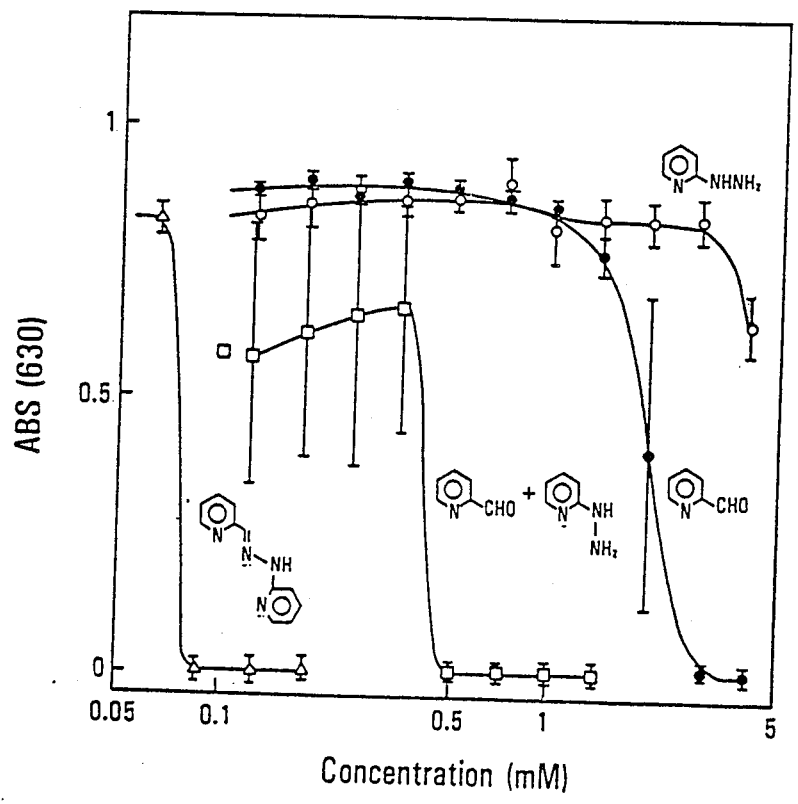
FIG. 8 shows the fungicidal effect of a self-assembling chelator.
Figure 9:
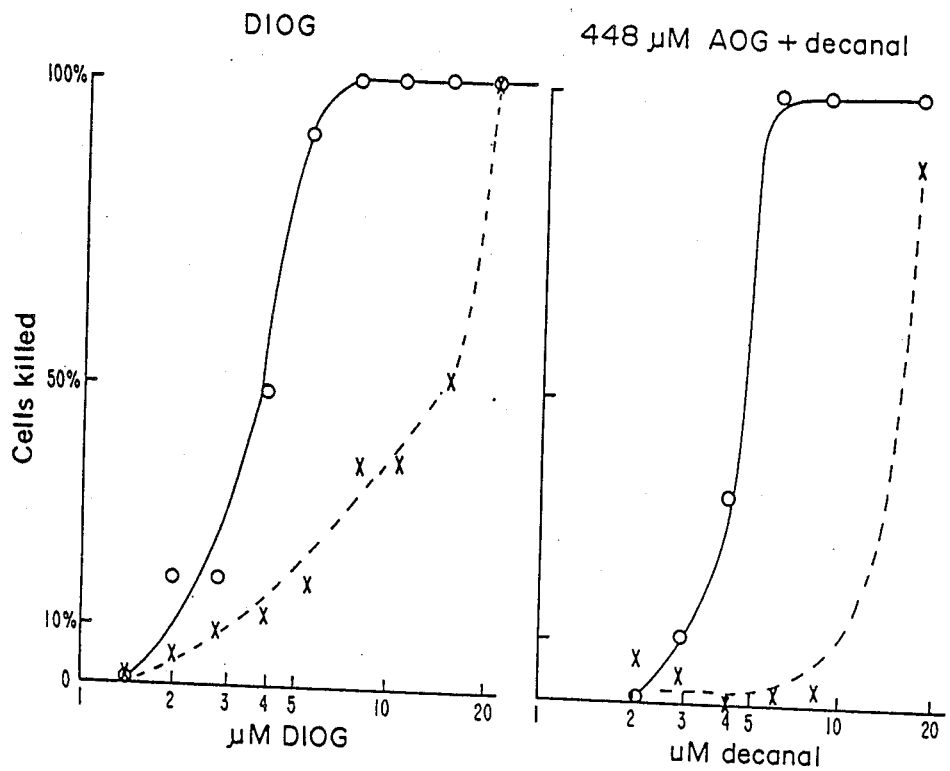
FIG. 9 shows amplification of the effect of serum on toxicity when the conjugate is administered as its component as compared to in its preformed state.

Similar results are obtained using Candida albicans, a human infective agent, as the target organism. These results are shown in FIG. 8; the fungistatic activity of the mixture is achieved at a concentration level for the components of 5× that of the product. Also, the growth of Monilinia sp, the causal agent in peach brown rot, is inhibited by the combination of the foregoing reagents, but not by either individually. No growth is observed after four days on YPD medium when 250 μM each of the pyridine-2-carboxaldehyde and 2-hydrazinopyridine are included. However, substantial growth is observed in a solution containing 2 mM of either reagent alone.

Salmonella

The formation of the foregoing chelate is also effective in inhibiting the growth of Salmonella typhimurium. This inhibition can be tested using agar disks or in culture suspension. The effect of the formation of chelate can be studied in this regard by conducting the experiments at pH 5 and pH 7.4; at pH 5 the formation of the chelate is encouraged while at pH 4 the reaction rate is much slower.

When tested by saturation of filter disks placed on a growing culture of S. typhimurium on agar LB plates, 20 nanomoles of the chelator PCPH inhibited growth at both pH 7.4 and pH 5. When similar plates were treated with separate disks containing 400 nanomoles HP on one disk and 400 nanomoles PC on the other, little inhibition was observed at pH 7.4, but at pH 5 growth inhibition exceeded that of the PCPH control. The inhibition was spread between the disks rather than circling each disk as was the case for the PCPH inhibition. Thus, control of pH is a selective factor in controlling the self-assembly of the cytotoxic chelator.

This selectivity was also shown in suspension cultures when S. typhimurium strain 14028R was incubated for 20 hours at 37° C. in PBS at either pH 5 or pH 7.4 containing 1% DMSO. When no drugs were added, the culture contained $8\times 10^6$ colony forming units (CFU)/ml for pH 5 and $1.5\times 10^7$ CFU/ml for pH 7.4. The self assembling drugs tested in this instance were semicarbazide (SC), 4-nitro-2-furaldehyde (NFA) and their reaction product nitrofurazone (NFZ). Either the NFC product, or mixtures of various concentrations of the precursors NC+NA were added after inoculation of the medium. While the maximum toxic selectivity (the ratio of CFU/ml at pH 7.4 as compared to CFU/ml at pH 5) observed for, NFZ alone, at 10 μM was about 100, a mixture of 1500 μM SC+7 μM gave a toxic selectivity ratio of over 8000.

Solubility

Because the components of a reaction may be individually soluble whereas the product is relatively insoluble, administration of the individual components may permit administration of higher dosages than would otherwise be possible. The PC and HP described above can be reacted to obtain supersaturated solutions of the reaction product PCPH.

EXAMPLE 2

Effect of Decanal and AOG on Various Organisms

Several types of target cells have been shown susceptible to treatment with the combination of decanal and N-amino-N-1-octylguanidine (AOG) together, as opposed to treatment with these materials singly. Together, the compounds were capable of destroying large quantities of cells; incubation with each separately was nontoxic. (Controls using 1-decanol instead of decanal in combination with AOG also showed no enhanced cytotoxicity.)

As described in detail below, AOG in combination with decanal shows a considerable potency in situ in lysis of erythrocytes and in exhibiting bactericidal activity against the human pathogen *E. coli* J96, as well as the HeLa cultured human tumor line, and in preventing the growth of yeast.

Erythrocytes

For erythrocytes, blood was collected and stored with KEDTA at 4° C. and erythrocytes prepared within 48 hours by centrifuging three times in phosphate-buffered saline (PBS, pH 7.4). Suspensions containing $3 \times 10^7$ cells/ml were prepared in PBS containing 1% EtOH, but no covalent cations, and incubated at 37° C. with the compounds or mixtures to be tested. A control assay was performed using 14 μM DIOG previously prepared, and complete lysis was obtained in 20 minutes.

Figure 2:
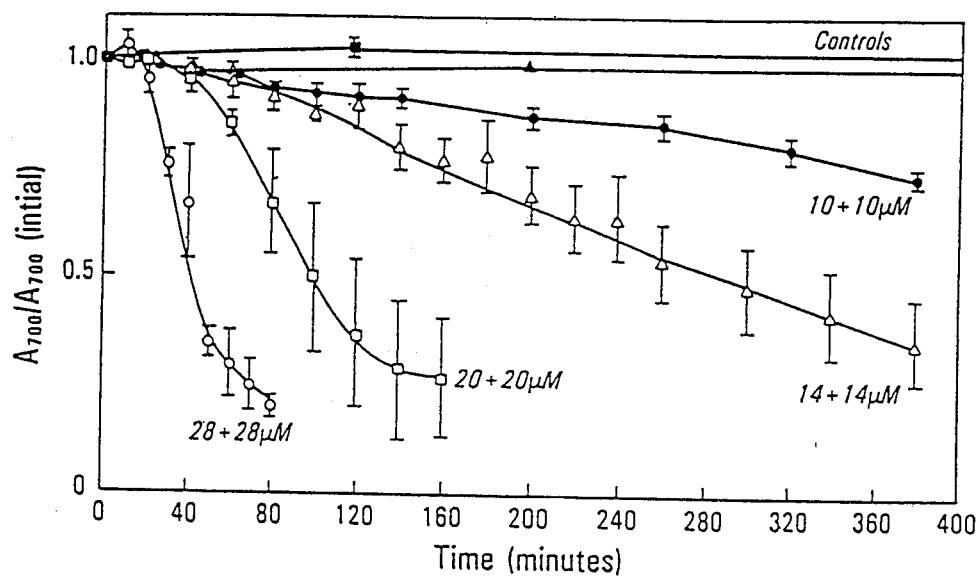
FIG. 2 shows the results of treating erythrocytes with AOG+decanal at various concentrations.

On the other hand, while a mixture of 28 μM AOG and 28 μM decanal (reagent grade, Aldrich Chemical Co.) results in less than 10% lysis within the same 20 minute time frame, as the time of incubation increases, lysis increases also, as indicated by hemoglobin release measured by (1) light absorption of the supernatant at 400 nm, (2) decrease of light scattering by the cells at 700 nm, and (3) direct cell counts using a microscope. This cytotoxic effect from the combination was shown to exhibit dose-response characteristics typical of cooperative effect of the two components, as further described below:

FIG. 2 shows, in more detail, results comparing the effect of mixtures of decanal and AOG with either alone on cell lysis. Suspensions of $3.5 \times 10^7$ cells/ml prepared as above in PBS (1% EtOH, no divalent cations, pH 7.4) were incubated at 37° C., and cell lysis was followed by observing the decrease in absorbance at 700 nm. For 0% lysis, $A_{700}$ is 1.0; 0.2 for 100% lysis).

As shown in FIG. 2, control experiments containing either (1) 28 μM or 80 μM decanal; or (2) 28 μM, 100 μM or 200 μM AOG, showed less than 5% lysis after more than 400 minutes. However, progressively higher concentrations in mixtures of the two components showed dramatic increases in efficiency. For a combination of 28 μM each of the components, 50% lysis was achieved after only 40 minutes, as compared with a much longer time frame for a mixture containing 10 μM in each component.

Figure 3:
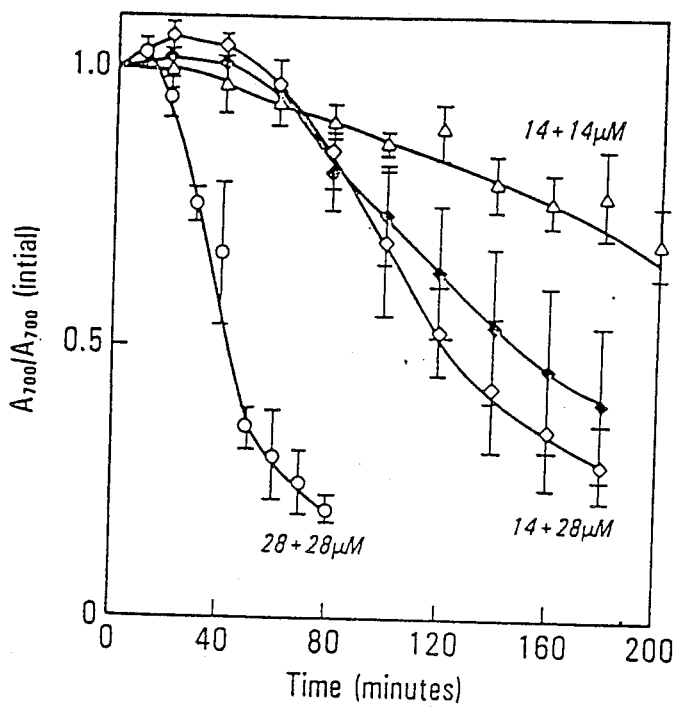
FIG. 3 shows the results on hemolysis of erythrocytes obtained when AOG and decanal are varied independently.

FIG. 3 shows the effect of independent variation of each component. Decreasing either the decanal concentration or the AOG concentration from 28 μM to 14 μM while holding the other constant results in approximately the same diminution in effectiveness.

In each of the foregoing groups of determinations, the presence or absence of the expected DIOG adduct was detected using thin layer chromatography after chloroform/methanol extraction of the erythrocytes. Suspensions treated with 28 μM each decanal and AOG showed the presence of DIOG. DIOG could not be detected in extracts of erythrocytes treated with either decanal or AOG alone under otherwise identical conditions.

Figure 4:
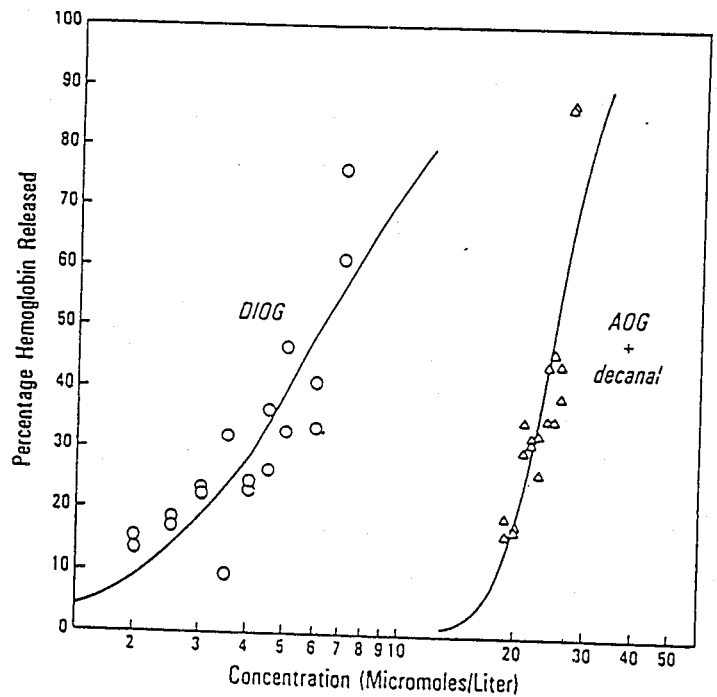
FIG. 4 shows dose response curves for hemoglobin release from human erythrocytes using AOG+decanal or their adduct, DIOG.

FIG. 4 shows the dose-response curves for hemoglobin release from human erythrocytes, prepared as above and monitored by increase in absorption at 400 nm. The curves were calculated using a nonlinear least squares fitting algorithm (Arc, H, et al, *Statistical Methods* (1970) Harper & Row, pp. 100-111) and based on a modified Hill equation (Cantor, C. R. et al, supra) wherein percent hemolysis is calculated as 100% divided by $1+(K/C)^\alpha$. In this equation, K is the median effect concentration, C is the concentration of DIOG (or of decanal and AOG), and α is the Hill constant.

DIOG gave a considerably lower median effect concentration (6.2 μM) than did decanal plus AOG (25 μM) however, the Hill constant for DIOG is approximately 2, as compared to 6.7 for the combination. The combination thus exhibits a much sharper dose-response curve, as would be expected from the requirement for combination of the two components in order to effect hemolysis.

Similar results were observed with respect to erythrocyte lysis when other combinations forming analogous hydrazones were used. For example, after 24 hours, only 18% lysis was observed in the presence of 60 mM cyclohexanedione (CHD) alone or in the presence of 3 mM 1,2-diamino-3-phenylguanidinium iodide (DAPG) alone. However, the combination of 5 mM CHD with 0.5 mM DAPG produced 76% lysis over the same time period. In addition, the combination of 25 μM each of decanedialdehyde, $CHO(CH_2)_8CHO$ (DDD) and AOG produced 100% lysis in erythrocytes after two hours, although either DDD or AOG alone at 100 μM did not result in any observable lysis.

Bacteria

A similar result was obtained in testing against *E. coli* J96. Table 1 gives the results of incubating decanal and AOG at physiological conditions (37° C., pH 7.4, PBS containing magnesium and calcium ion) for 20 hr on the number of viable bacteria per ml.

TABLE 1

| μM Decanal | μM AOG | Viable Bacteria/ml |
|---|---|---|
| 0 | 0 | $2 \times 10^8$ |
| 200 | 0 | $5 \times 10^8$ |
| 400 | 0 | $5 \times 10^8$ |
| 0 | 200 | $3 \times 10^8$ |
| 0 | 400 | $2 \times 10^7$ |
| 200 | 200 | $8 \times 10^5$ |
| 400 | 400 | <10 |

The combination of 200 μM each of decanal and AOG resulted in a diminution of viable bacteria from $200 \times 10^6$/ml to $0.8 \times 10^6$ per ml, and the combination of 400 μM each of these reagents resulted in less than 10 viable bacteria per ml. In contrast, similar concentrations of either reagent alone resulted in substantially no bactericidal effect, although 400 μM AOG reduced the number of viable bacteria per ml tenfold.

HeLa Cells

The results for HeLa cell cytotoxicity are shown in FIG. 5. These cells were grown in suspension in Joklik's median supplemented with calf serum, centrifuged and then taken up into Dulbecco's modified Eagles medium (DMEM) without serum. Cell suspensions containing $2-4 \times 10^6$ cell/ml in DMEM containing 1% ethanol were incubated at 37° C., with or without decanal, AOG, or combinations thereof. Cell membrane damage was measured by hand counting of cells using trypan blue exclusion as the criterion.

Figure 5B:
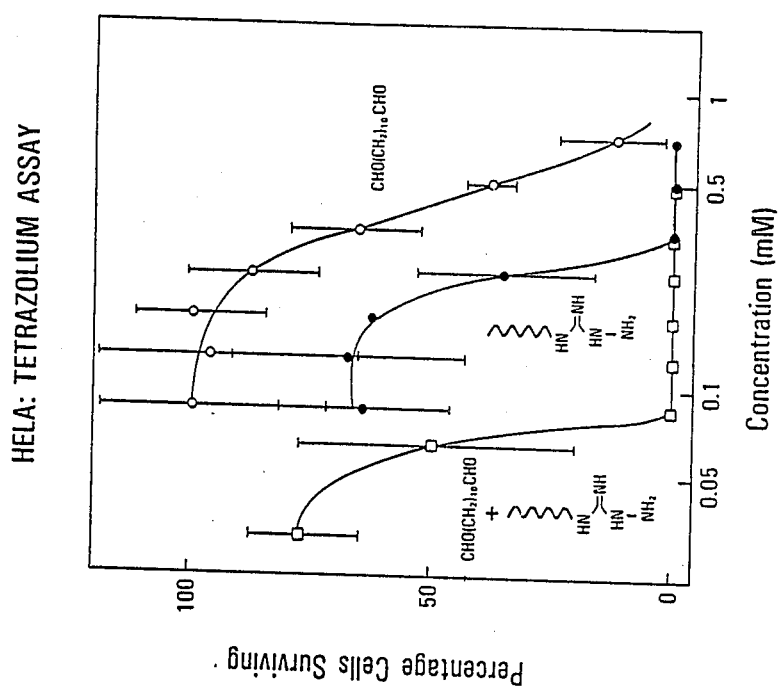
FIG. 5b shows the HeLa cell toxicity of combinations of AOG and dodecanedial.
Figure 5A:
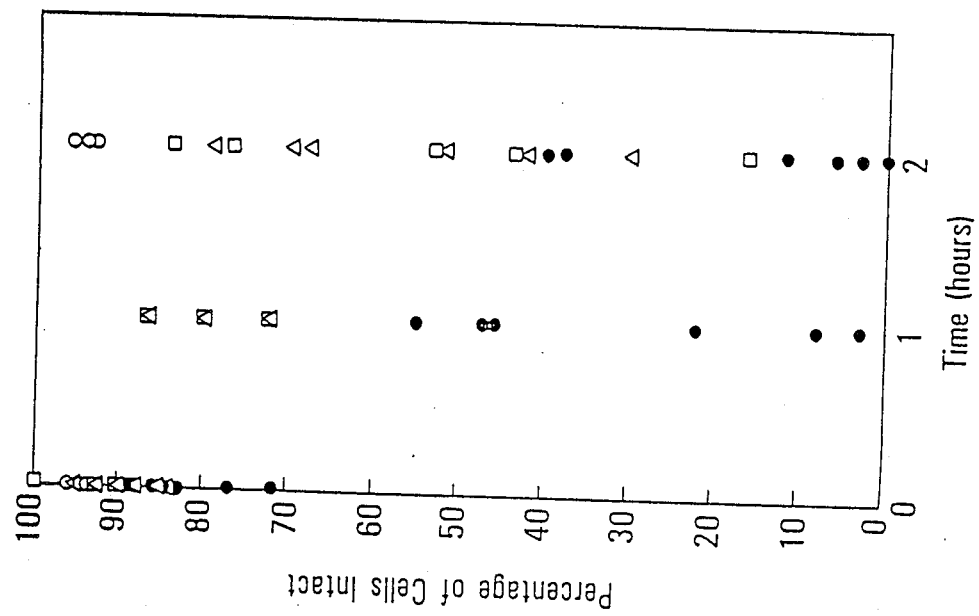
FIG. 5a shows the HeLa cell toxicity of combinations of AOG and decanal.

In FIG. 5a, the dark circles representing a mixture of 200 μM decanal plus 200 μM AOG show a dramatic decrease in percentage of cells intact over the course of two hours. However, the open circles which represent control cells containing no reagents remained almost 100% intact after two hours. The open squares representing 400 μM decanal and open triangles representing 400 μM AOG, each alone, resulted in considerably less dramatic decreases in cell concentration than the combination of 200 μM each.

Results of a similar experiment, using dodecandial are shown in FIG. 5b; only the combination of AOG and dodecanedial is effective, neither is very toxic alone.

Yeast

The effect of the combination of AOG and decanal on yeast was also determined. S. cerevisiae in YPD medium at cell densities of $10^5$–$10^6$ cell/ml used as starting concentrations. When no reagents were added to the medium, the cell density increased about 90 fold in 24 hours. When 20 μg/ml decanal was added to the medium, an 11 fold increase was observed; when 88 μg/ml AOG was added a threefold increase occurred. When 10 μg/ml decanal plus 44 μg/ml AOG were added in combination, all yeast died after 24 hours.

EXAMPLE 3

Effect of Solvent Conditions

The kinetics of the reaction between AOG and decanal were studied in micellar surfactant solutions. Concentrations of 280 μM decanal plus 28 μM AOG, where good pseudo first order kinetics were obtained, were used. The reaction was run in SDS alone, in the presence of octyl-β-D-glucopyranoside (ODG) and in a medium containing both SDS and ODG. The results are shown in Table 2.

TABLE 2

| Condition | k(Sec-1) |
|---|---|
| 10 mM SDS | $10 \times 10^{-4}$ |
| 20 mM ODG | $7 \times 10^{-5}$ |
| 10 mMSDS + 20 mMODG | $6 \times 10^{-4}$ |

EXAMPLE 4

Antidotes to Self Assembly

The formation of the toxic conjugate can be controlled by the use of an antidote. Host cells which selectively accumulate the antidote will be protected from the toxic effects of the assembled biologically active agent in comparison to target cells which do not. The use of antidotes to protect nontarget cells is known in the art; for example, Leucovorin is often administered to counteract methotrexate treatment used against cancer; diethyl thiocarbamate protects normal tissue against cis platinium (Bodenner, D. L., et al, Cancer Res (1986) 46: 2745–2750).

In this example, cyclohexanone is used as an antidote to prevent the assembly of AOG plus decanal to produce the biologically active agent DIOG, which was described in a previous example. Erythrocytes, prepared as above, were exposed to 20 μM AOG plus 20 μM decanal. With no pretreatment, or with a pretreatment consisting of 2 hours of incubation with 20 mM cyclohexanone alone, extensive lysis occurred. Extensive lysis was also obtained when the cells were first exposed to 20 μM AOG for 2 hours and then treated with 20 μM decanal and 20 mM cyclohexanone.

However, pretreatment for 2 hours with 20 mM cyclohexanone plus 20 μM AOG resulted in only slow lysis when 20 μM decanal was then added. (20 mM cyclohexanone plus 10 μM AOG alone do not give lysis.) Presumably, the cyclohexanone combines with at least a portion of the AOG to obtain a nonlytic concentration of adduct, which inhibits subsequent DIOG formation from decanal and AOG.

EXAMPLE 5

Use of Rhodamine-Derived Precursors to Confer Selective Concentration

Since rhodamine is known to have an affinity for carcinoma cells, precursors analogous to those of Example 2, but containing rodamine-derived moieties associated with the carbonyl and hydrazine functionalities are used as precursors, wherein the rhodamine nucleus of the formula

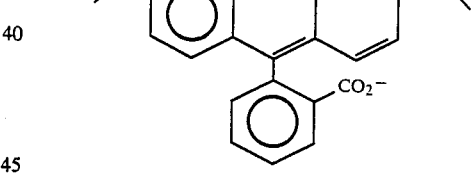

is modified to contain the desired functionality. The reaction of RD2 and RD5, RD1 and RD9, and of RD4 and RD3 result in single adducts RM1, RM2 and RM3; the reaction of RD10 and RD12 results in a polymer. These reactions are shown in Reaction Scheme 6 below.

For in vitro testing, EJ human bladder carcinoma cells are spread at low density in DMEM in tissue culture flasks and treated with, for example, RD2 or RD5 individually at varying concentrations from 0.3–100 μM for incubation periods of 2–24 hours at 37° C. in 5% CO$_2$. The cells are then washed, incubated, and counted for colony-forming units (CFU). The results are then compared with treatment of the cells under similar conditions using similar but lower concentrations of RD2 plus RD5 in combination.

To confirm the synthesis of the adduct RM1 by the cells, RM1 prepared synthetically is used as a chromatographic standard, and the presence of RM1 in cells treated with RD2 plus RD5 shown in butanol extracts using standard chromatographic techniques.

Comparison of selectivity of combination for malignant and nonmalignant cells is demonstrated using the monkey kidney nontumorogenic cell line BSC1 in control experiments in comparison to mouse breast carcinoma CCL51, as described for the EJ human bladder carcinoma cells above.
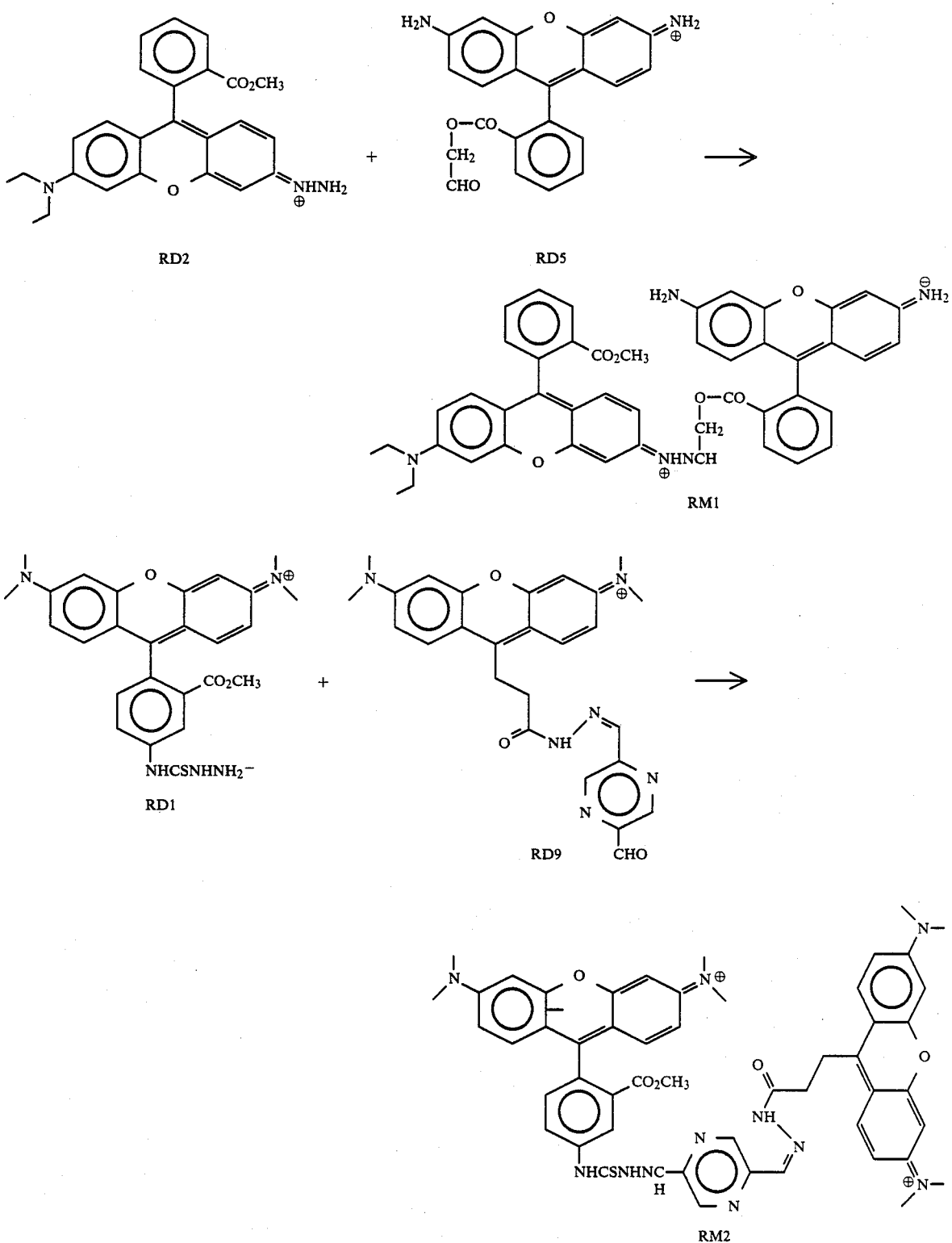
Reaction Scheme 6

-continued
Reaction Scheme 6
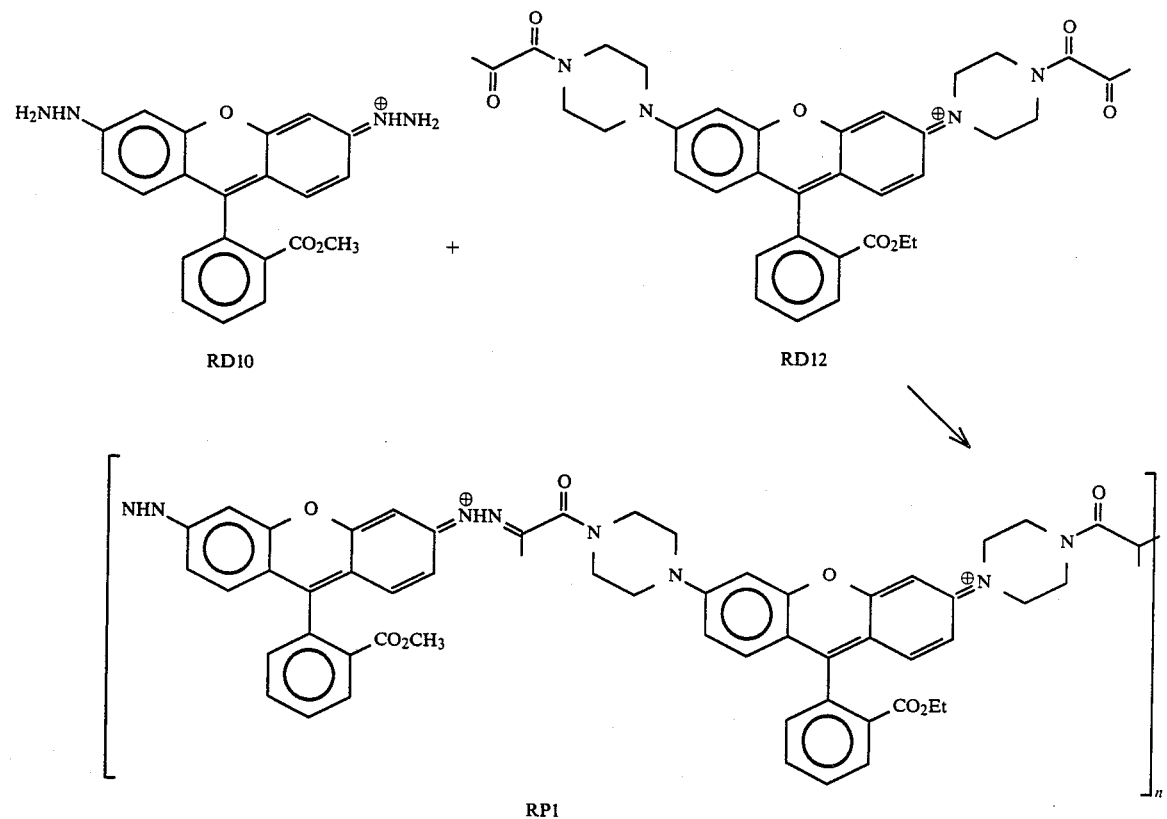
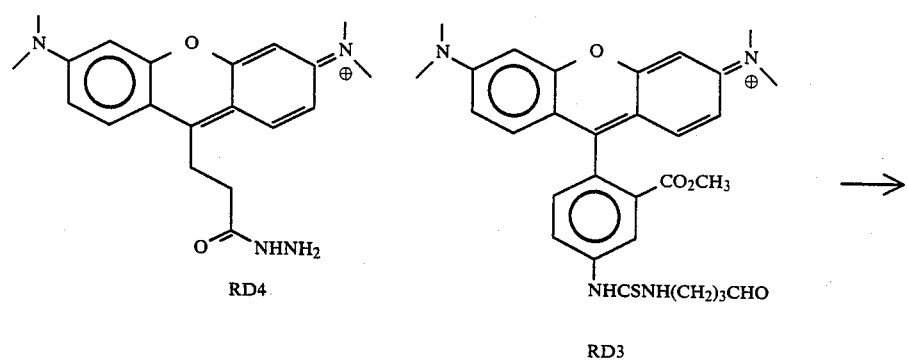
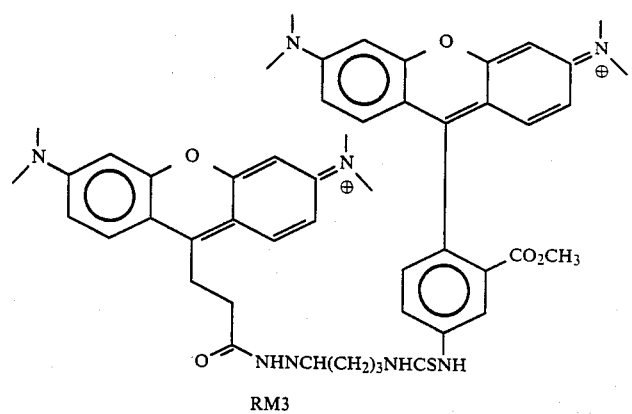

EXAMPLE 6

Effect of the Presence of Serum on Potency of Self-Assembled Active Agents

Comparisons were made of the capacities of the mixtures of dodecanedial and AOG at various concentrations to effect killing of HeLa cells in the presence and absence of serum. The cells to be tested were incubated for five hours in the presence of various concentrations of mixtures of dodecanedial and AOG either with or without 50% serum added to the reacton mixture. After 5 hours of incubation, 50% serum was added to the serum-free reaction mixture and an additional 18 hours incubation was conducted.

As shown from the results in Table 1 below, when serum was absent during the initial incubation, cell killing became effective at much lower concentrations than that exhibited by the components added to the cells in the presence of serum.

TABLE 1

| AOG + Dodecanedial | % cells killed (50% serum) | % cells killed (0% serum) |
|---|---|---|
| 31 + 31 μM | 0,0 | 6,8 |
| 50 + 50 μM | 0 | 50 |
| 63 + 63 μM | 0,6 | 0,5 |
| 125 + 125 μM | 31,12 | 100,100 |
| 155 + 155 μM | 47 | 100 |
| 250 + 250 μM | 67,92 | 100,100 |
| 500 + 500 μM | 100,100 | 100,100 |

This result was verified using lower serum concentrations, as low as 1%. In these experiments, the effect appeared much more dramatic when the components (AOG and decanal) were supplied separately than when the assumed active conjugate (DIOG) was added directly instead of permitting its formation in situ.

Ox blood erythrocytes were incubated for one hour in PBS at pH 6.6 in the presence or absence of 1% serum at 37° C. With 1% serum present, there was no cell killing even at 2 μM DIOG. However, at 4–16 μM DIOG, the percentage of cells killed increased from 4.3 to 60.9. On the other hand, in the absence of serum, 7.2.% cells were killed even without the addition of DIOG, and a steady increase in killing occurred as the DIOG concentration increased, reaching 100% of cells killed at 8 μM. These results are shown in Table 2 below. A similar experiment extending to higher concentrations of DIOG gave similar results as shown in Table 3.

TABLE 2

| DIOG | % cells killed (0% serum) | % cells killed (1% serum) |
|---|---|---|
| 16 μM | 100 | 60.9 |
| 8 | 100 | 29 |
| 4 | 47.8 | 4.3 |
| 2 | 29 | 0 |
| 1 | 10.1 | 0 |
| 0 | 7.2 | 0 |

TABLE 3

| DIOG | % Cells Killed (0% Serum) | % Cells Killed (1% Serum) |
|---|---|---|
| 32 μM | 100 | 98.7 |
| 22.4 | 100 | 100 |
| 16 | 100 | 51.3 |
| 11.2 | 100 | 37.2 |
| 8 | 100 | 35.9 |
| 5.6 | 91 | 16.7 |
| 4 | 48.7 | 11.5 |
| 2.8 | 17.9 | 9 |
| 2 | 17.9 | 5.1 |
| 1.4 | 1.3 | 0 |
| 0 | 0 | 0 |

Table 4 shows an analogous experiment conducted using the precursors of DIOG rather than the product. The AOG concentration was maintained at a high level (448 μM) and the decanal concentration varied from 0–16 μM corresponding the previous DIOG concentration range. In this protocol, similar results were obtained for cells incubated in the absence of serum, but in the presence of 1% serum the curve was slightly displaced so that the cells appeared more protected as shown in Table 4.

TABLE 4

| Decanal | % cells killed (0% serum) | % cells killed (1% serum) |
|---|---|---|
| 0 μM* | 6.4 | 1.3 |
| 16 μM | 78.2 | 100 |
| 8 | 2.6 | 100 |
| 5.6 | 1.3 | 100 |
| 4 | 0 | 34.6 |
| 2.8 | 5.1 | 11.5 |
| 2 | 7.7 | 1.3 |
| 0 | 0 | 0 |

*896 μM AOG

Table 5 shows results of analogous experiments using 448 μM AOG where cell killing was measured by hemaglobin release rather than light scattering as in the results shown in Tables 2–4.

TABLE 5

| Decanal Concentration | 1% Serum | No Serum |
|---|---|---|
| 0* | 0 | 4.6,3.7 |
| 448 | 1.6,1.1 | 7.3,5.8 |
| 22.4 | 99.7,99.6 | 100,95.2 |
| 16 | 17.5,12.6 | 100,96.8 |
| 13.5 | 8.1,6.4 | 100,96.4 |
| 11.2 | 2.1,1 | 100,99.6 |
| 8 | 0,0 | 99.8,99.3 |
| 6.7 | 0,0 | 85.8,85.6 |
| 5.6 | 0,0 | 57.9,74.4 |
| 4.7 | 0,0 | 21.6,24.1 |
| 4 | 0,0 | 14.9,10.1 |
| 3.4 | 0,0 | 6.4,8.4 |
| 2.8 | 0,0 | 5.7,5.3 |
| 2.35 | 0,0 | 2.9,1.7 |
| 2 | 0,0 | 1,1.7 |
| 1.4 | 0,0 | 0.4,1.6 |
| 0 | 0,0 | 0,4.8 |

*896 μM AOG

The results of Tables 3 and 4 which offer a direct comparison of results when components are administered as compared to when the conjugate is administered are shown in FIG. 10.

As shown from the foregoing results, serum not only protects cells from the effects of DIOG, but this effect is amplified when the DIOG is formed in situ from its components.

Figure 10B:
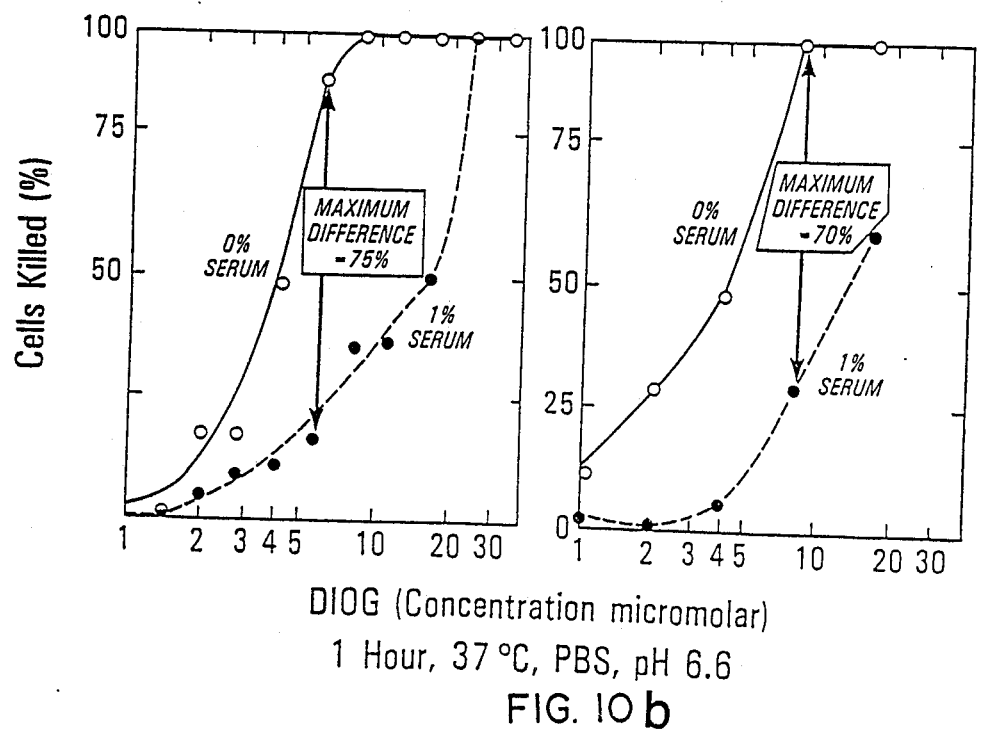

The results are even more dramatically shown by comparing graphical representations of the foregoing results. In FIG. 10a, varying amounts of decanal are supplied in the presence of 448 μM AOG in the presence of no serum or of 1% serum. As shown in that figure, decanal dosages which are 100% effective in the absence of serum have *no* effect when serum at 1% is present. Thus a complete selectivity between conditions wherein serum is present and absent can be achieved. On the other hand, as shown in FIG. 10b, when the product of AOG and decanal is provided pre-assembled, there are no decanal concentrations at which a 100% difference in reactivity can be achieved.

One possible explanation for this effect, by which explanation Applicant does not intend to be bound, is that the serum is capable of inhibiting the biological activity at two levels—both at the level of the biologically active agent and at the level of preventing its formation.

EXAMPLE 7

Effect on Ox Erythrocytes—Temperature Selectivity

Figure 11:
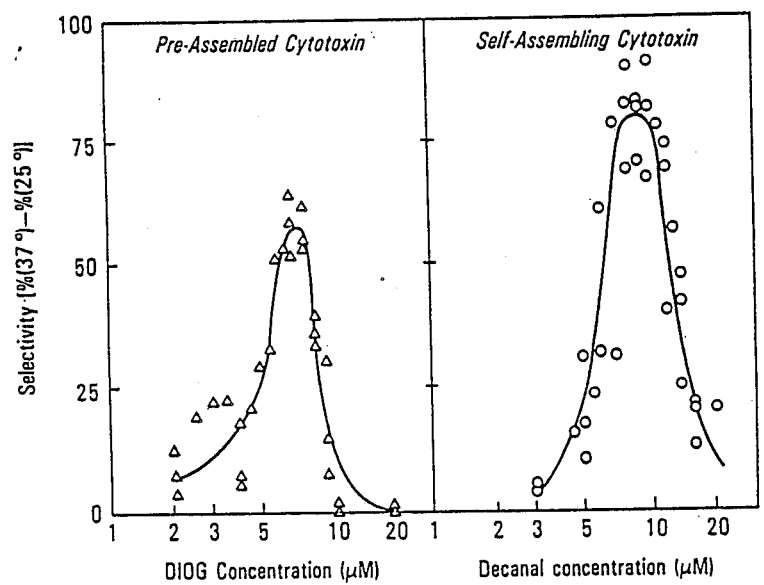

The preassembled DIOG and and combination of AOG with decanal at various concentrations was tested at two different temperatures. The erythrocytes were incubated at 37° C. or 25° C. in the presence of 448 μM AOG, pH 6 in varying concentrations of decanal or were incubated with various concentrations of preassembled DIOG. The destruction of the erythrocytes was measured by a hemoglobin release and the ratio of release at 37° and 25° was determined. The results of this comparison are shown in FIG. 11 which plots the DIOG concentration or decanal concentration against the selectivity representing the difference between hemolysis at 37° and 25° C. At the optimum concentration of decanal, the temperature sensitivity for the mixture is considerably higher than that at the optimum concentration of DIOG as shown in the Figure.

I claim:

1. A method to modify a target condition contained within an environment with a conjugate active in modifying said target condition which conjugate comprises at least two components
   which method comprises providing said environment with said components, which may be the same or different
   wherein said components become covalently bonded to obtain the conjugate active in modifying said target condition when in the microenvironment of the target condition.

2. The method of claim 1 which is effective to localize selectively the effect of said conjugate on said target condition.

3. The method of claim 2 wherein the selective localization is achieved by accessibility of the microenvironment to the components as compared to the conjugate combined with ability of the microenvironment to prevent the release of the conjugate.

4. The method of claim 1 wherein said components selectively become covalently conjugated to obtain the conjugate in the microenvironment of the target condition.

5. The method of claim 4 wherein at least one of the components is selectively concentrated in the microenvironment of the target condition.

6. The method of claim 5 wherein the selective concentration is achieved by the microenvironment being preferentially attractive to said component.

7. The method of claim 6 wherein the microenvironment comprises tumor cells.

8. The method of claim 7 wherein at least one component contains a residue selected from the group consisting of rhodamine, uroporphyrin, and hematoporphyrin.

9. The method of claim 5 wherein the selective concentration is achieved by the microenvironment being capable of binding covalently to said component.

10. The method of claim 5 wherein the selective concentration is achieved by the microenvironment being differentially capable of activating said component.

11. The method of claim 5 wherein the selective concentration is achieved by the microenvironment being differentially incapable of inactivating said component.

12. The method of claim 4 wherein the microenvironment of the target condition is differentially favorable for the covalent bonding of the components to form said conjugate.

13. The method of claim 1 wherein the microenvironment comprises tumor cells.

14. The method of claim 1 wherein the conjugate is a hydrazone.

15. The method of claim 1 wherein the conjugate is an o-substituted oxime.

16. The method of claim 1 wherein the conjugate is a polyionic polymer.

17. The method of claim 1 wherein the conjugate is DIOG.

18. A pharmaceutical composition containing at least two components which are differentially capable in the microenvironment of a target condition as compared to the surroundings of said target condition, to bond covalently to form a conjugate active in modifying said target condition.

* * * * *